(12) United States Patent
Bokinsky et al.

(10) Patent No.: US 9,902,964 B2
(45) Date of Patent: Feb. 27, 2018

(54) GROWTH ARRESTED CELLS USEFUL FOR PRODUCING COMPOUNDS

(71) Applicant: The Regents of the University of California, Oakland, CA (US)

(72) Inventors: Gregory E. Bokinsky, Delft (NL); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/709,328

(22) Filed: May 11, 2015

(65) Prior Publication Data

US 2015/0353939 A1    Dec. 10, 2015

Related U.S. Application Data

(60) Provisional application No. 61/991,404, filed on May 9, 2014.

(51) Int. Cl.
| | |
|---|---|
| *C12N 1/21* | (2006.01) |
| *C12N 15/70* | (2006.01) |
| *C12N 15/10* | (2006.01) |
| *C12N 15/64* | (2006.01) |
| *C12N 15/65* | (2006.01) |
| *C12N 15/66* | (2006.01) |
| *C12N 9/12* | (2006.01) |

(52) U.S. Cl.
CPC ............... *C12N 15/70* (2013.01); *C12N 9/12* (2013.01); *C12N 15/10* (2013.01); *C12N 15/64* (2013.01); *C12N 15/65* (2013.01); *C12N 15/66* (2013.01)

(58) Field of Classification Search
None
See application file for complete search history.

(56) References Cited

U.S. PATENT DOCUMENTS

| 5,871,922 A | 2/1999 | Salmond et al. |
|---|---|---|
| 2004/0038250 A1 | 2/2004 | Nunez et al. |

FOREIGN PATENT DOCUMENTS

WO        9532294 A1     11/1995

OTHER PUBLICATIONS

Alexander C, Bilgin N, Lindschau C, Mesters Jr, Kraal B, Hilgenfeld R, Erdmann VA, Lippmann C. 1995. Phosphorylation of elongation factor Tu prevents ternary complex formation. J. Biol. Chem. 270:14541-14547.
Allison KR, Brynildsen MP, Collins JJ. 2011. Heterogeneous bacterial persisters and engineering approaches to eliminate them. Curr. Opin. Microbiol. 14:593-598.
Allison KR, Brynildsen MP, Collins JJ. 2011. Metabolite-enabled eradication of bacterial persisters by aminoglycosides. Nature 473:216-220.
Balaban NQ, Merrin J, Chait R, Kowalik L, Leibler S. 2004. Bacterial persistence as a phenotypic switch. Science 305:1622-1625.
Bokinsky et al., Hip-A-Triggered growth arrest and B-Lactam tolerance in *Escherichia coli* are mediated by RelA-Dependent ppGpp synthesis., J. of Bacteriology, V 195, No. 14, 3173-3182. (2013).
Brown L, Gentry D, Elliott T, Cashel M. 2002. DksA affects ppGpp induction of RpoS at a translational level. J. Bacteriol. 184:4455-4465.
Thristensen SK, Gerdes K. 2004. Delayed-relaxed response explained by hyperactivation of RelE. Mol. Microbiol. 53:587-597.
Correia FF, D'Onofrio A, Rejtar T, Li LY, Karger BL, Makarova K, Koonin EV, Lewis K. 2006. Kinase activity of overexpressed HipA is required for growth arrest and multidrug tolerance in *Escherichia coli*. J. Bacteriol. 188:8360-8367.
Ferullo DJ, Lovett ST. 2008. The stringent response and cell cycle arrest in *Escherichia coli*. PLoS Genet. 4:e1000300.
Gerdes K, Maisonneuve E. 2012. Bacterial persistence and toxin-antitoxin loci. Annu. Rev. Microbiol. 66:103-123.
Haseltine WA, Block R. 1973. Synthesis of guanosine tetra- and pentaphosphate requires the presence of a codon-specific, uncharged transfer ribonucleic acid in the acceptor site of ribosomes. Proc. Natl. Acad. Sci. U. S. A. 70:1564-1568.
Heath RJ, Jackowski S, Rock CO. 1994. Guanosine tetraphosphate inhibition of fatty acid and phospholipid synthesis in *Escherichia coli* is relieved by overexpression of glycerol-3-phosphate acyltransferase (plsB). J. Biol. Chem. 269:26584-26590.
Kanjee U, Ogata K, Houry WA. 2012. Direct binding targets of the stringent response alarmone (p) ppGpp. Mol. Microbiol. 85:1029-1043.
Kasari V, Mets T, Tenson T, Kaldalu N. 2013. Transcriptional cross-activation between toxin-antitoxin systems of *Escherichia coli*. BMC Microbiol. 13:4510.1186/1471-2180-13-45.
Keren I, Kaldalu N, Spoering A, Wang YP, Lewis K. 2004. Persister cells and tolerance to antimicrobials. FEMS Microbiol. Lett. 230:13-18.
Korch SB, Hill TM. 2006. Ectopic overexpression of wild-type and mutant hipA genes in *Escherichia coli*: effects on macromolecular synthesis and persister formation. J. Bacteriol. 188:3826-3836.
Korch SB, Henderson TA, Hill TM. 2003. Characterization of the hipA7 allele of *Escherichia coli* and evidence that high persistence is governed by (p)ppGpp synthesis. Mol. Microbiol. 50:1199-1213.
Lewis K. 2010. Persister cells. Annu. Rev. Microbiol. 64:357-372.
Maciag M, Kochanowska M, Lyzen R, Wegrzyn G, Szalewska-Palasz A. 2010. ppGpp inhibits the activity of *Escherichia coli* DnaG primase. Plasmid 63:61-67.
Maisonneuve E, Shakespeare LJ, Jorgensen MG, Gerdes K. 2011. Bacterial persistence by RNA endonucleases. Proc. Natl. Acad. Sci. U. S. A. 108:13206-13211.
McKee AE, Rutherford BJ, Chivian DC, Baidoo EK, Juminaga D, Kuo D, Benke Pi, Dietrich JA, Ma SM, Arkin AP, Petzold CJ, Adams PD, Keasling JD, Chhabra SR. 2012. Manipulation of the carbon storage regulator system for metabolite remodeling and biofuel production in *Escherichia coli*. Microb. Cell Fact. 11:7910. 1186/1475-2859-11-79.

(Continued)

*Primary Examiner* — Jim Ketter
(74) *Attorney, Agent, or Firm* — Robin C. Chiang; Lawrence Berkeley National Laboratory

(57) ABSTRACT

The present invention provides for a genetically modified host cell in a growth-arrested state producing an antibiotic.

14 Claims, 9 Drawing Sheets

(56) References Cited

OTHER PUBLICATIONS

Moyed HS, Broderick SH. 1986. Molecular cloning and expression of hipA, a gene of *Escherichia coli* K-12 that affects frequency of persistence after inhibition of murein synthesis. J. Bacteriol. 166:399-403.

Moyed HS, Bertrand KP. 1983. hipA, a newly recognized gene of *Escherichia coli* K-12 that affects frequency of persistence after inhibition of murein synthesis. J. Bacteriol. 155:768-775.

Nguyen D, Joshi-Datar A, Lepine F, Bauerle E, Olakanmi O, Beer K, McKay G, Siehnel R, Schafhauser J, Wang Y, Britigan BE, Singh PK. 2011. Active starvation responses mediate antibiotic tolerance in biofilms and nutrient-limited bacteria. Science 334:982-986.

Potrykus K, Murphy H, Philippe N, Cashel M. 201t ppGpp is the major source of growth rate control in *E. coli*. Environ. Microbiol. 13:563-575.

Rodionov DG, Ishiguro EE 1995. Direct correlation between overproduction of guanosine 3',5'-bispyrophosphate (ppGpp) and penicillin tolerance in *Escherichia coli*. J. Bacteriol. 177:4224-4229.

Schumacher MA, Piro KM, Xu W, Hansen S, Lewis K, Brennan RG. 2009. Molecular mechanisms of HipA-mediated multidrug tolerance and its neutralization by HipB. Science 323:396-401.

Svitil AL, Cashel M, Zyskind JW. 1993. Guanosine tetraphosphate inhibits protein synthesis in vivo. A possible protective mechanism for starvation stress in *Escherichia coli*. J. Biol. Chem. 268:2307-2311.

Vazquez-Laslop et al., Increased persistence in *Escherichia coli* caused by controlled expression of toxins or other unrelated proteins., J. Bacteriology. V. 188, No. 10, 3494-3497. (2006).

Wang JD, Sanders GM, Grossman AD. 2007. Nutritional control of elongation of DNA replication by (p) ppGpp. Cell 128:865-875.

Yamaguchi Y, Inouye M. 2011. Regulation of growth and death in *Escherichia coli* by toxin-antitoxin systems. Nat. Rev Microbiol. 9:779-790.

Zaslaver A, Bren A, Ronen M, Itzkovitz S. Kikoin I, Shavit S, Liebermeister W, Surette MG, Alon U. 2006. A comprehensive library of fluorescent transcriptional reporters for *Escherichia coli*. Nat Methods 3:623-628.

A

B

GROWTH ARRESTED CELLS USEFUL FOR PRODUCING COMPOUNDS

CROSS-REFERENCE TO RELATED APPLICATIONS

This application claims priority to U.S. Provisional Patent Application Ser. No. 61/991,404, filed on May 9, 2014, which is hereby incorporated by reference.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the field of using growth-arrested cells as platforms for production of antibiotics.

BACKGROUND OF THE INVENTION

In 2013, antibiotic resistant bacteria were responsible for an estimated 2 million illnesses and at least 23,000 deaths in the United States alone {(CDC), 2013 #1948}. Diversification of our antibiotic arsenal is crucial for counteracting the spread of resistance and ensuring our ability to effectively treat bacterial infections. The vast majority of antibiotics, whose structural complexity presents a considerable challenge to chemical synthesis, are produced industrially by engineered microbial hosts {Elander, 2003 #1943; Hamed, 2013 #1882}. Unfortunately, many species cannot be successfully engineered to produce antibiotics at amounts sufficient for an industrial process. For many compounds, biosynthesis pathways can be transferred to genetically-tractable, well-established industrial production species such as Escherichia coli {Keasling, 2010 #166}, which can be further modified with enzymes from different biosynthetic pathways, potentially generating enormous diversity {Weeks, 2011 #1840}. Unfortunately, this solution is not readily available to antibiotic manufacture due to the obvious toxicity of the compounds: the host cells would be destroyed by their products.

Persister cells are bacteria in a transient, growth-arrested state that provides tolerance of multiple classes of antibiotics (1, 2). The ability to resist antibiotic treatment enables persister cells to sustain bacterial infections. The persistent state, which likely describes a number of different growth-arrested physiologies (3), has been at least partially attributed to the activity of toxin/antitoxin (TA) modules (4). TA modules are composed of two genes; one of the two genes encodes a toxin protein whose expression slows or stops cell growth, and the other encodes its corresponding antitoxin protein or RNA, which either inactivates its toxin directly or prevents translation of the toxin protein. Toxins have diverse enzymatic activities and cellular targets (5), and it is thought that active toxins trigger the growth slowdown or arrest that is characteristic of the persistent state by inhibiting a central cellular process. A link between TA modules and persistence has recently been demonstrated in a laboratory setting using Escherichia coli MG1655. In that study, deletion of five or more chromosomally encoded TA modules reduced the number of persister cells generated (6).

The first toxin protein to be linked to persistence in E. coli was the serine/threonine kinase HipA (7), which forms a TA module with its cognate antitoxin, HipB. HipA overexpression within growing E. coli bacteria causes multiple responses that are the hallmarks of persistence, including growth arrest and tolerance of certain classes of antibiotics, as well as attenuation of DNA replication, transcription, and translation (8). Some insight into the mechanism of HipA-induced growth arrest was gained when it was discovered that HipA phosphorylates the protein EF-Tu (9), an essential translation factor that catalyzes the binding of aminoacyl-tRNA to the ribosome. Phosphorylation by HipA is expected to deactivate EF-Tu (10), which may account for the inhibition of translation within HipA-arrested cells. How HipA expression also inhibits DNA and RNA synthesis and provides tolerance of certain antibiotics when translation is inhibited is unclear. Translational inhibition is insufficient to explain the general arrest of macromolecular synthesis, as translation inhibition by other means (e.g., by addition of the ribosome inhibitor chloramphenicol) does not inhibit DNA replication or RNA transcription (11) or provide antibiotic tolerance (12). While it is possible that HipA inhibits DNA and rRNA synthesis directly, such as by phosphorylating protein targets other than EF-Tu, we and others have observed that the growth arrest triggered by HipA is similar to the effects of the alarmone guanosine tetraphosphate (ppGpp) (8). ppGpp allosterically inhibits enzymes that are central to an incredible variety of cellular processes in E. coli, including priming of DNA replication (13), rRNA transcription (14), translation (15), phospholipid synthesis (16), and certain metabolic enzymes (17). A link between the stringent response and persistence has been postulated on the basis of the finding that an E. coli strain lacking the enzymes required to synthesize ppGpp (RelA and SpoT) generates fewer persister cells (18). One possible interpretation of this finding might be that ppGpp is necessary for inducing a cellular response, such as expression of toxins or degradation of antitoxins, that triggers persistence upon application of stress. An alternative explanation is that ppGpp directly confers resistance by inhibiting cellular processes itself (18), an aspect of regulation by ppGpp that is often unappreciated (19). Understanding the mechanisms by which toxin activity leads to growth arrest and antibiotic tolerance is critical for informing efforts to eradicate persisters (3).

SUMMARY OF THE INVENTION

The present invention provides for a genetically modified host cell in a growth-arrested state producing an antibiotic.

The present invention provides for a genetically modified host cell, comprising: (a) increased expression of a toxin of a toxin-antitoxin (TA) module, or a substantially identical polypeptide thereof, (b) increased expression of one or more enzymes of a pathway for the biosynthesis of an antibiotic that is toxic to the host cell when the host cell is growing, and (c) optionally reduced expression of an endogenous RelA.

In some embodiments, the TA module is the HipA-HipB and the toxin is HipA, or a substantially identical polypeptide thereof.

The genetically modified host cell is a bacterium that has been engineered or modified by human action. In some embodiments, the one or more enzymes of a pathway for the biosynthesis of an antibiotic are heterologous to the host cell. The antibiotic can be any individual antibiotic of an antibiotic family or individual antibiotic described herein. In some embodiments, the antibiotic is carbapenem, thienamycin, or penicillin.

In some embodiments, the pathway derived or obtained from the "Car" pathway, comprising CarA, B, C, D and E from *Pectobacter carotovorum* (taught in WO 1995032294 A1, and U.S. Pat. No. 5,871,922), and the thienamycin pathway from *Streptomyces cattleya* (taught in U.S. Patent Application Pub. No. US 2004/0038250 A1).

The present invention provides for a method of constructing the genetically modified host cell comprising (a) introducing a first vector encoding the toxin, or a substantially identical polypeptide thereof, operatively linked to a promoter capable of expressing the toxin in the host cell, one or more enzymes of a pathway for the biosynthesis of an antibiotic into the host cell, (b) optionally introducing a second vector encoding the one or more enzymes of the pathway for the biosynthesis of the antibiotic into the host cell operatively linked to one or more promoters capable of expressing the enzymes in the host cell, and (c) optionally disrupting an endogenous relA gene in the host cell.

The present invention provides for a method of producing an antibiotic comprising: (a) providing the genetically modified host cell, (b) arresting the growth of the host cell, and (c) producing the antibiotic.

The term "increased expression" can mean a native gene having its expression increased, or the presence of a heterologous gene in the host cell, or both. Expression can be increased by having the expression increased (by the substitution of a stronger promoter or activating DNA sequences that increase expression of the promoter), or introducing one or more copies of the native, or one or more heterologous, gene each operably linked to a promoter into the host cell, such that the expression of the gene is increased constitutively or under certain growth conditions.

The term "reduced expression" can mean a native gene having its promoter and/or open reading frame (ORF) altered such that the expression of the wild-type, or active, enzyme or gene product is reduced under all or certain growth conditions. In some embodiments, the native gene is knocked out in that the host cell does not or essentially does not express the gene at all. In some embodiments, the promoter is completely or partially deleted, or the ORF is completely or partially deleted from the host cell's genome.

When an enzyme is described in the present invention, the scope of the invention includes enzymes, including non-naturally or engineered enzymes having an amino acid sequence having at least 50% identity to the amino acid sequence of a naturally occurring or known enzyme, wherein the enzyme, including non-naturally or engineered enzyme, retains all conserved amino acid residues essential for its enzymatic activity, and has an enzymatic activity that is at least all or substantially all of the naturally occurring or known enzyme.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
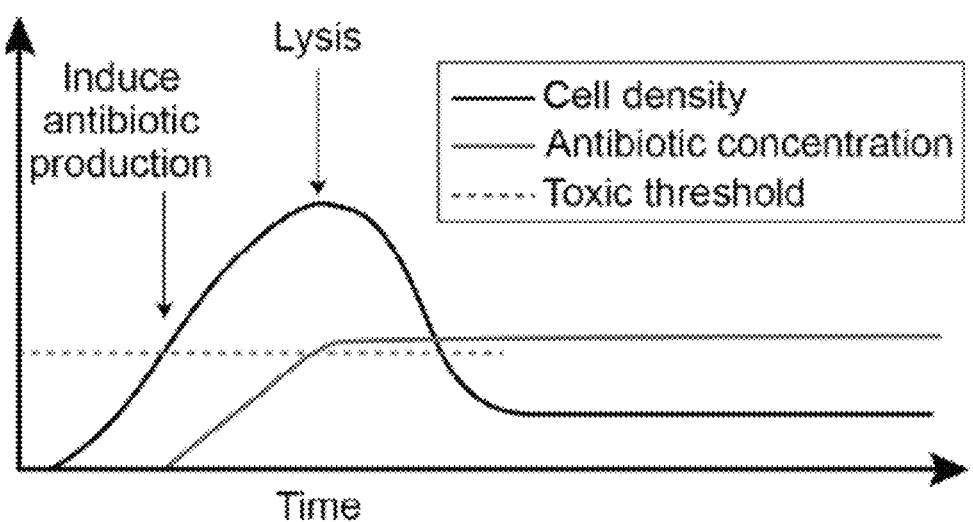
FIG. 1 shows the use of growth-arrested cells as a platform for antibiotic production. Panel (A): production of cell wall-targeting antibiotics in sensitive bacteria results in cell lysis, which limits the amount of antibiotic that can be produced. Panel (B): Induction of growth arrest by expression of the HipA toxin inactivates cell wall biogenesis while maintaining overall metabolic activity, allowing cells to resist antibiotic toxicity and enabling production to continue.
Figure 1:
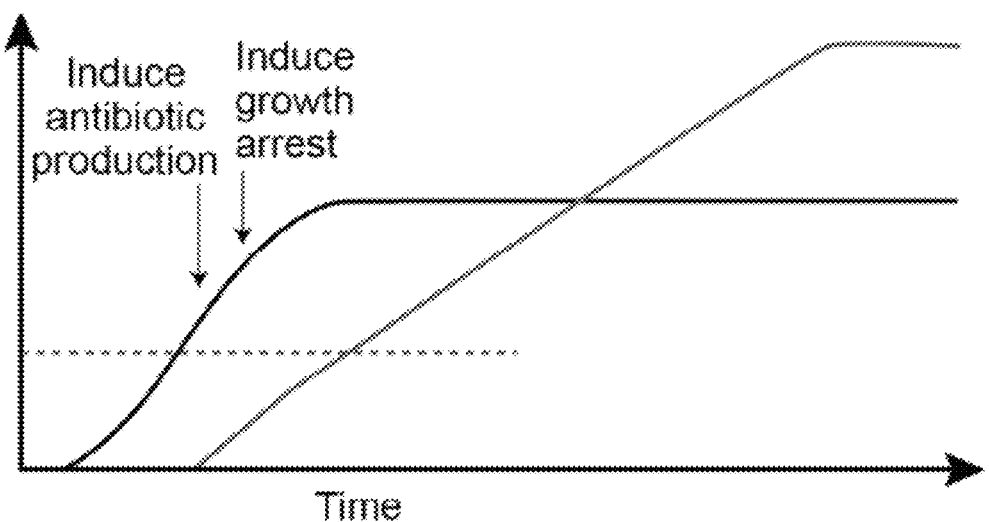
Figure 2:
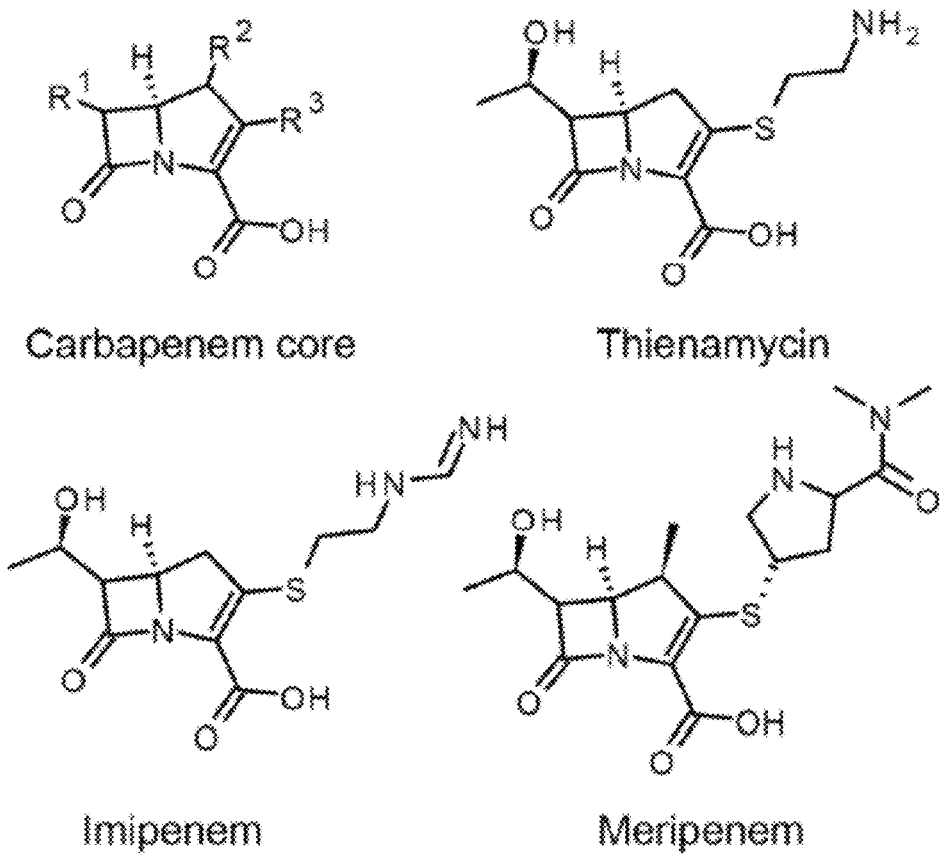
FIG. 2 shows the chemical structure of carbapenem family of antibiotics, including the clinically-available derivatives, imipenem and meripenem.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

As used herein, the term "enzyme" or any of the named enzymes encompasses polymorphic variants, alleles, mutants, and interspecies homologs to the specific polypeptides described herein or known to those skilled in the art. A nucleic acid that encodes an enzyme refers to a gene, pre-mRNA, mRNA, and the like, including nucleic acids encoding polymorphic variants, alleles, mutants, and interspecies homologs of the particular amino acid sequences described herein. Thus, in some embodiments, an enzyme encodes a polypeptide having an amino acid sequence that has at least 50% amino acid sequence identity, or at least 55%, 60%, 65%, 70%, 75%, 80%, 85%, 90%, or in particular 91%, 92%, 93%, 94%, 95%, 96%, 97%, 98% or 99% or greater amino acid sequence identity, preferably over a region of at least about 25, 50, 100, 200 or more amino acids, or over the length of the entire polypeptide, to any one of the amino acid sequences shown herein.

The terms "increased expression," "increased level of activity," or "increased activity" refer interchangeably to an increase in the amount of activity of the enzyme in an engineered host cell compared to the amount of activity in a wild-type (i.e., naturally occurring) host cell. In some embodiments, increased activity results from increased expression levels. An increased level of activity or increased level of expression can be an increase in the amount of activity or expression of the enzyme in a cell genetically modified to overexpress the enzyme of at least 10%, 20%, 30%, 40%, 50%, 60%, 70%, 80%, or 90% or greater compared to a wildtype cell. Increased expression or activity of an enzyme can be assessed by any number of assays, including, but not limited to, the methods described in Examples 1 and 2.

The terms "reduced expression", "reduced level of activity", "reduced activity", and "decreased activity" refer interchangeably to a reduction in the amount of activity of the enzyme in a cell engineered to decrease the enzyme compared to the amount of activity in a wild-type (i.e., naturally occurring) cell. In some embodiments, reduced activity results from reduced expression levels. A reduced level of activity or a reduced level of expression can be a reduction in the amount of activity or expression of the enzyme of at least 10%, 20%, 30%, 40%, 50%, 60%, 70%, 80%, or 90% or greater. In some embodiments, the enzyme is not reduced in amount, but is modified in amino acid sequence so that its activity is reduced directly or indirectly. Decreased expression or activity of the gene encoding the enzyme can be assessed by any number of assays, including, but not limited to, the methods described in Examples 1 and 2.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 70% sequence identity with a reference sequence. Percent identity can be any integer from 70% to 100%. Some embodiments include at least: 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. For example, a polynucleotide encoding an enzyme may have a sequence that is at least 70%, 75%, 80%, 85%, 90%, 91%, 92%, 93%, 94%, 95%, 96%, 97%, 98%, or 99% identical to a sequence of an enzyme identified herein.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are illustrative conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). (see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

An enzyme or polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, RNAi, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding an enzyme operably linked to a heterologous promoter.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

These and other objects, advantages, and features of the invention will become apparent to those persons skilled in the art upon reading the details of the invention as more fully described below.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter. (See deBoer et al. (1983) *Proc. Natl. Acad. Sci. USA,* 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: bacterial plasmids. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. The host cell can be transformed with at least one expression vector. When only a single expression vector is used (without the addition of an intermediate), the vector will contain all of the nucleic acid sequences necessary.

The enzyme described herein can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

The invention provides for a method to harness the metabolically-active cell stasis for production of valuable small molecules that are toxic to actively growing cells, such as beta-lactam antibiotics, especially the carbapenem family. While there are many methods for inducing ppGpp production, inducing expression of the toxin of a toxin-antitoxin (TA) module, such as HipA, is particularly straightforward. Furthermore, ppGpp-mediated growth arrest provides nearly complete protection from certain cell wall-targeting compounds, and other compounds that are toxic to growing cells (but not compounds that interfere with the RelA pathway). Production of valuable antibiotics in genetically-tractable species will open up opportunities for metabolic engineering to increase production titers. Furthermore, it is likely that arrested cells for production is less expensive than alternatives such as cell-free systems. This will be particularly useful for antibiotic compounds that are produced in low amounts by organisms that are not amenable to being grown to high cell densities in bioreactors. It may also lower the production costs of compounds that are only cost-effective to produce using synthetic chemistry.

Figure 5:
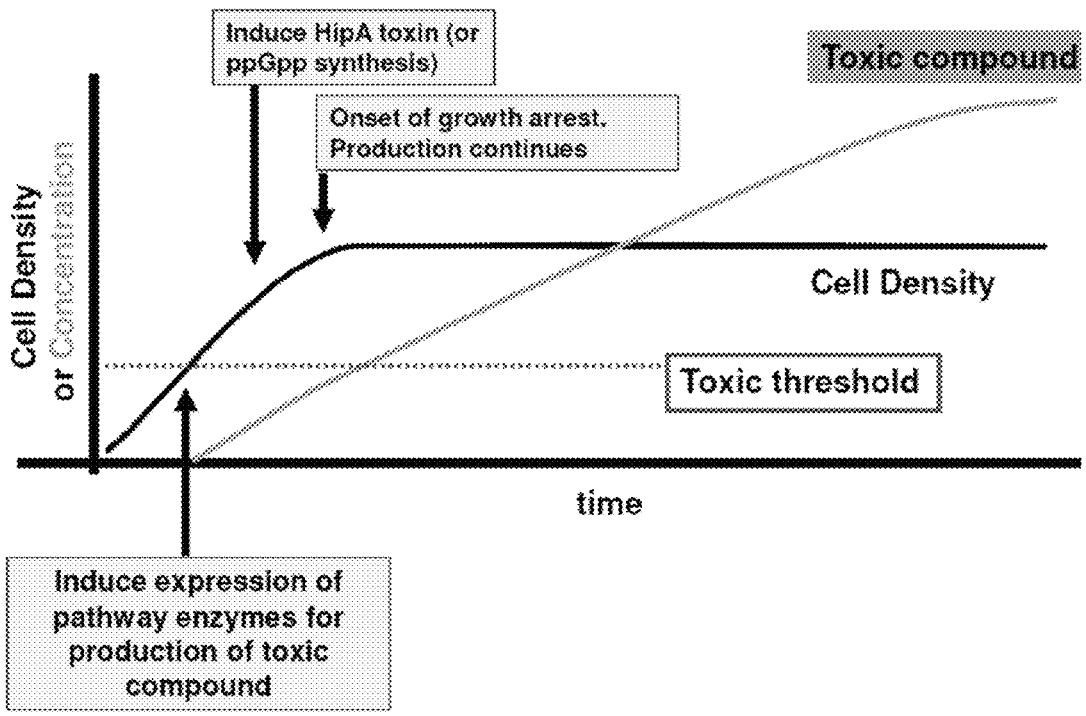
FIG. 5 shows the use of growth-arrested cells as a platform for antibiotic production.
Figure 6:
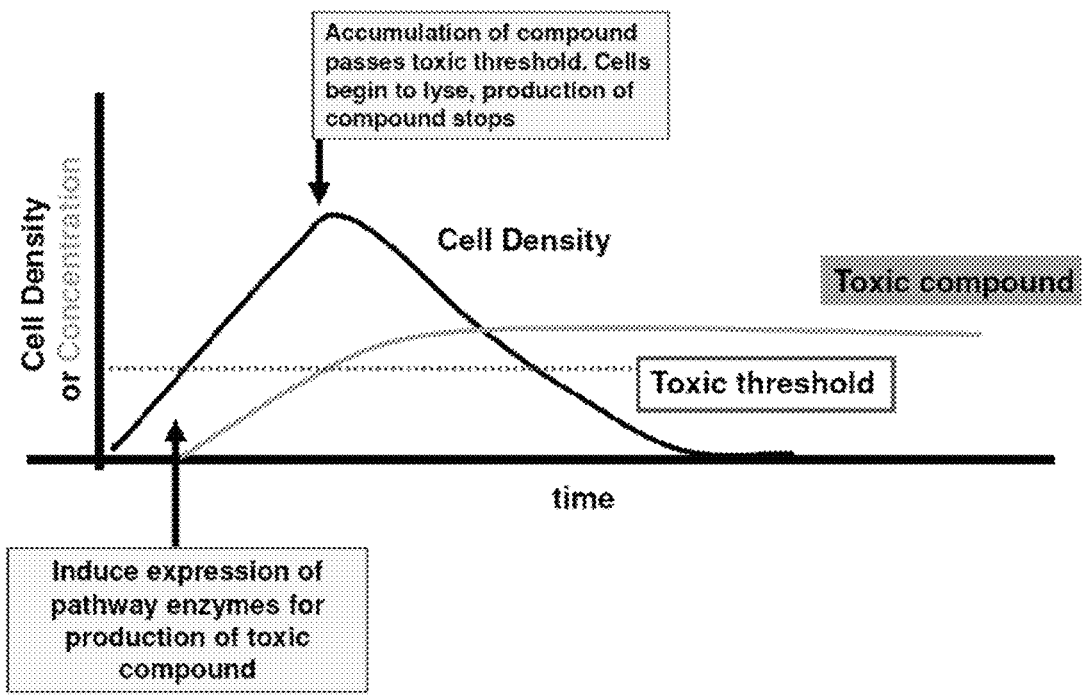
FIG. 6 shows the growth curve of cells that is producing antibiotic that is toxic to the cell.

The method of using the toxin of a toxin-antitoxin (TA) module, using HipA as an example, is as follows (see FIGS. 5 and 6). Cells are grown in medium and the production pathway for the toxic molecule is induced, after which the pathway enzymes build up inside the cell and production of the toxic compound is started. After an interval determined by the rate of production and the concentration of compound that is toxic to the producers (the interval could be zero), the toxin HipA is induced, triggering protective cell stasis.

Meanwhile, as cell stasis does not affect the central metabolism of the arrested cells (such as carbon or nitrogen intake), or the activity of the pathway enzymes, production of the toxic compound will continue.

The amino acid sequence of *E. coli* HipA is:

```
                                                    (SEQ ID NO: 1)
        10         20         30         40         50
MPKLVTWMNN QRVGELTKLA NGAHTFKYAP EWLASRYARP LSLSLPLQRG 60         70         80         90        100
NITSDAVFNF FDNLLPDSPI VRDRIVKRYH AKSRQPFDLL SEIGRDSVGA 110        120        130        140        150
VTLIPEDETV THPIMAWEKL TEARLEEVLT AYKADIPLGM IREENDFRIS 160        170        180        190        200
VAGAQEKTAL LRIGNDWCIP KGITPTTHII KLPIGEIRQP NATLDLSQSV 210        220        230        240        250
DNEYYCLLLA KELGLNVPDA EIIKAGNVRA LAVERFDRRW NAERTVLLRL 260        270        280        290        300
PQEDMCQTFG LPSSVKYESD GGPGIARIMA FLMGSSEALK DRYDFMKFQV 310        320        330        340        350
FQWLIGATDG HAKNFSVFIQ AGGSYRLTPF YDIISAFPVL GGTGIHISDL 360        370        380        390        400
KLAMGLNASK GKKTAIDKIY PRHFLATAKV LRFPEVQMHE ILSDFARMIP 410        420        430        440
AALDNVKTSL PTDFPENVVT AVESNVLRLH GRLSREYGSK
```

In some embodiments, a substantially identical polypeptide of HipA comprises one or more of the following conserved residues or regions:

| Feature | Position(s) | Description |
| --- | --- | --- |
| Binding site | 181 | ATP |
| Active site | 309 | Proton acceptor |
| Nucleotide binding | 152-157 | ATP |
| Nucleotide binding | 234-236 | ATP |
| Nucleotide binding | 311-314 | ATP |
| Nucleotide binding | 331-332 | ATP |
| DNA binding | 379-382 | |

Variations on this approach can be imagined. If the concentration at which the compound is toxic to the cells is extremely low, a portion of the pathway responsible for intermediate production steps can be induced, and induction of the rest of the pathway can be co-induced with expression of HipA. Furthermore, as translation is not completely inhibited by HipA, it is possible to imagine inducing the remaining pathway after HipA induction.

Nearly all bacteria possess genes called toxin-antitoxin modules. Expression of toxin proteins in excess of their cognate antitoxin protein (or RNA) results in temporary growth arrest. While their roles in bacterial physiology and ecology are unclear at present, the diverse mechanisms by which they trigger growth arrest are becoming clear. We and others have studied the toxin HipA (NCBI Reference Number NC_000913.2), found in the species *Escherichia coli*, and determined the mechanism by which it triggers growth arrest. HipA is a toxin protein that phosphorylates the aminoacyl-tRNA synthetase GltX (Gerdes 2013), rendering the protein unable to charge its cognate tRNA with the amino acid glutamate. This generates a pool of uncharged tRNAGlu, which bind to the ribosome, triggering synthesis of a compound known as guanosine tetraphosphate by the ribosome-associated protein RelA, a response widely known as the stringent response. The molecule ppGpp is known to attenuate translation, transcription, DNA replication, and phospholipid biosynthesis. Inhibition of phospholipid biosynthesis deactivates steps involved in peptidoglycan biogenesis. As a consequence of this inhibition, cell becomes tolerant of antibiotics that target cell wall biogenesis, such as beta-lactam antibiotics (ampicillin and carbenicillin), which are in widespread medical usage. Thus, cells with a functioning RelA enzyme are capable of entering into a HipA-facilitated cell stasis. We have also demonstrated (Bokinsky 2013) that cells in this stasis have an active metabolism that can be harnessed for the production of molecules through heterologous pathways. HipA-arrested cells produced mevalonate for nearly one week in the presence of high concentrations (100 mg/L) of the antibiotic ampicillin.

Companies that manufacture costly antibiotics (such as the carbapenem family of antibiotics, currently synthesized using total organic synthesis) could conceivably use this for economical production of valuable bacteriocidal antibiotics within a genetically-tractable host that has good GRAS status and is commonly used in fermenters. This technology could also be used as a research platform for in vivo determination of enzyme activities on toxic substrates (understanding the roles of enzymes in antibiotic production pathways, for instance)

REFERENCES CITED

1. Balaban N Q, Merrin J, Chait R, Kowalik L, Leibler S. 2004. Bacterial persistence as a phenotypic switch. Science 305:1622-1625.
2. Lewis K. 2010. Persister cells. Annu. Rev. Microbiol. 64:357-372.
3. Allison K R, Brynildsen M P, Collins J J. 2011. Heterogeneous bacterial persisters and engineering approaches to eliminate them. Curr. Opin. Microbiol. 14:593-598.
4. Gerdes K, Maisonneuve E. 2012. Bacterial persistence and toxin-antitoxin loci. Annu. Rev. Microbiol. 66:103-123.
5. Yamaguchi Y, Inouye M. 2011. Regulation of growth and death in *Escherichia coli* by toxin-antitoxin systems. Nat. Rev. Microbiol. 9:779-790.

6. Maisonneuve E, Shakespeare L J, Jorgensen M G, Gerdes K. 2011. Bacterial persistence by RNA endonucleases. Proc. Natl. Acad. Sci. U.S.A 108:13206-13211.
7. Moyed H S, Broderick S H. 1986. Molecular cloning and expression of hipA, a gene of *Escherichia coli* K-12 that affects frequency of persistence after inhibition of murein synthesis. J. Bacteriol. 166:399-403.
8. Korch S B, Hill T M. 2006. Ectopic overexpression of wild-type and mutant hipA genes in *Escherichia coli*: effects on macromolecular synthesis and persister formation. J. Bacteriol. 188:3826-3836.
9. Schumacher M A, Piro K M, Xu W, Hansen S, Lewis K, Brennan R G. 2009. Molecular mechanisms of HipA-mediated multidrug tolerance and its neutralization by HipB. Science 323:396-401.
10. Alexander C, Bilgin N, Lindschau C, Mesters J R, Kraal B, Hilgenfeld R, Erdmann V A, Lippmann C. 1995. Phosphorylation of elongation factor Tu prevents ternary complex formation. J. Biol. Chem. 270:14541-14547.
11. Wisseman C L, Jr, Smadel J E, Hahn F E, Hopps H E. 1954. Mode of action of chloramphenicol. 1. Action of chloramphenicol on assimilation of ammonia and on synthesis of proteins and nucleic acids in *Escherichia coli*. J. Bacteriol. 67:662-673.
12. Rodionov D G, Ishiguro E E. 1996. Dependence of peptidoglycan metabolism on phospholipid synthesis during growth of *Escherichia coli*. Microbiology 142(Pt 10):2871-2877.
13. Maciag M, Kochanowska M, Lyzen R, Wegrzyn G, Szalewska-Palasz A. 2010. ppGpp inhibits the activity of *Escherichia coli* DnaG primase. Plasmid 63:61-67.
14. Cashel M, Gallant J. 1969. Two compounds implicated in the function of the RC gene of *Escherichia coli*. Nature 221:838-841.
15. Svitil A L, Cashel M, Zyskind J W. 1993. Guanosine tetraphosphate inhibits protein synthesis in vivo. A possible protective mechanism for starvation stress in *Escherichia coli*. J. Biol. Chem. 268:2307-2311.
16. Heath R J, Jackowski S, Rock C O. 1994. Guanosine tetraphosphate inhibition of fatty acid and phospholipid synthesis in *Escherichia coli* is relieved by overexpression of glycerol-3-phosphate acyltransferase (plsB). J. Biol. Chem. 269:26584-26590.
17. Gallant J A. 1979. Stringent control in *Escherichia coli*. Annu. Rev. Genet. 13:393-415.
18. Korch S B, Henderson T A, Hill T M. 2003. Characterization of the hipA7 allele of *Escherichia coli* and evidence that high persistence is governed by (p)ppGpp synthesis. Mol. Microbiol. 50:1199-1213.
19. Kanjee U, Ogata K, Houry W A. 2012. Direct binding targets of the stringent response alarmone (p) ppGpp. Mol. Microbiol. 85:1029-1043.
20. Allison K R, Brynildsen M P, Collins J J. 2011. Metabolite-enabled eradication of bacterial persisters by aminoglycosides. Nature 473:216-220.
21. Redding-Johanson A M, Batth T S, Chan R, Krupa R, Szmidt H L, Adams P D, Keasling J D, Lee T S, Mukhopadhyay A, Petzold C J. 2011. Targeted proteomics for metabolic pathway optimization: application to terpene production. Metab. Eng. 13:194-203.
22. Tsuruta H, Paddon C J, Eng D, Lenihan J R, Horning T, Anthony L C, Regentin R, Keasling J D, Renninger N S, Newman J D. 2009. High-level production of amorpha-4,11-diene, a precursor of the antimalarial agent artemisinin, in *Escherichia coli*. PLoS One 4:e4489.10.1371/journal.pone.0004489
23. Lee T S, Krupa R A, Zhang F, Hajimorad M, Holtz W J, Prasad N, Lee S K, Keasling J D. 2011. BglBrick vectors and datasheets: a synthetic biology platform for gene expression. J. Biol. Eng. 5:12.10.1186/1754-1611-5-12
24. Horton R M, Cai Z L, Ho S N, Pease L R. 1990. Gene splicing by overlap extension: tailor-made genes using the polymerase chain reaction. Biotechniques 8:528-535.
25. Bennett B D, Yuan J, Kimball E H, Rabinowitz J D. 2008. Absolute quantitation of intracellular metabolite concentrations by an isotope ratio-based approach. Nat. Protoc. 3:1299-1311.
26. Buckstein M H, He J, Rubin H. 2008. Characterization of nucleotide pools as a function of physiological state in *Escherichia coli*. J. Bacteriol. 190:718-726.
27. Potrykus K, Murphy H, Philippe N, Cashel M. 2011. ppGpp is the major source of growth rate control in *E. coli*. Environ. Microbiol. 13:563-575.
28. Anderlei T, Zang W, Papaspyrou M, Büchs J. 2004. Online respiration activity measurement (OTR, CTR, R Q) in shake flasks. Biochem. Eng. J. 17:187-194.
29. McKee A E, Rutherford B J, Chivian D C, Baidoo E K, Juminaga D, Kuo D, Benke P I, Dietrich J A, Ma S M, Arkin A P, Petzold C J, Adams P D, Keasling J D, Chhabra S R. 2012. Manipulation of the carbon storage regulator system for metabolite remodeling and biofuel production in *Escherichia coli*. Microb. Cell Fact. 11:79.10.1186/1475-2859-11-79
30. Juminaga D, Baidoo E E K, Redding-Johanson A M, Batth T S, Burd H, Mukhopadhyay A, Petzold C J, Keasling J D. 2012. Modular engineering of L-tyrosine production in *Escherichia coli*. Appl. Environ. Microbiol. 78:89-98.
31. Yuan J, Bennett B D, Rabinowitz J D. 2008. Kinetic flux profiling for quantitation of cellular metabolic fluxes. Nat. Protoc. 3:1328-1340.
32. Keren I, Kaldalu N, Spoering A, Wang Y P, Lewis K. 2004. Persister cells and tolerance to antimicrobials. FEMS Microbiol. Lett. 230:13-18.
33. Lund E, Kjeldgaard N O. 1972. Metabolism of guanosine tetraphosphate in *Escherichia coli*. Eur. J. Biochem. 28:316-326.
34. Ferullo D J, Lovett S T. 2008. The stringent response and cell cycle arrest in *Escherichia coli*. PLoS Genet. 4:e1000300.
35. Rodionov D G, Ishiguro E E. 1995. Direct correlation between overproduction of guanosine 3',5'-bispyrophosphate (ppGpp) and penicillin tolerance in *Escherichia coli*. J. Bacteriol. 177:4224-4229.
36. Rodionov D G, Pisabarro A G, Depedro M A, Kusser W, Ishiguro E E. 1995. Beta-lactam-induced bacteriolysis of amino acid-deprived *Escherichia coli* is dependent on phospholipid synthesis. J. Bacteriol. 177:992-997.
37. Vázquez-Laslop N, Lee H, Neyfakh A A. 2006. Increased persistence in *Escherichia coli* caused by controlled expression of toxins or other unrelated proteins. J. Bacteriol. 188:3494-3497.
38. Pearl S, Gabay C, Kishony R, Oppenheim A, Balaban N Q. 2008. Nongenetic individuality in the host-phage interaction. PLoS Biol. 6:e120.10.1371/journal.pbio.0060120
39. Jones D T, Shirley M, Wu X, Keis S. 2000. Bacteriophage infections in the industrial acetone butanol (AB) fermentation process. J. Mol. Microbiol. Biotechnol. 2:21-26.
40. Junker B, Lester M, Leporati J, Schmitt J, Kovatch M, Borysewicz S, Maciejak W, Seeley A, Hesse M, Connors N, Brix T, Creveling E, Salmon P. 2006. Sustainable reduction of bioreactor contamination in an industrial fermentation pilot plant. J. Biosci. Bioeng. 102:251-268.
41. Los M, Czyz A, Sell E, Wegrzyn A, Neubauer P, Wegrzyn G. 2004. Bacteriophage contamination: is there a simple method to reduce its deleterious effects in laboratory cultures and biotechnological factories? J. Appl. Genet. 45:111-120.
42. Keasling J D. 2010. Manufacturing molecules through metabolic engineering. Science 330:1355-1358.
43. Kirby J, Keasling J D. 2009. Biosynthesis of plant isoprenoids: perspectives for microbial engineering. Annu. Rev. Plant Biol. 60:335-355.
44. Peralta-Yahya P P, Keasling J D. 2010. Advanced biofuel production in microbes. Biotechnol. J. 5:147-162.
45. Moyed H S, Bertrand K P. 1983. hipA, a newly recognized gene of *Escherichia coli* K-12 that affects frequency of persistence after inhibition of murein synthesis. J. Bacteriol. 155:768-775.
46. Rotem E, Loinger A, Ronin I, Levin-Reisman I, Gabay C, Shoresh N, Biham O, Balaban N Q. 2010. Regulation of phenotypic variability by a threshold-based mechanism underlies bacterial persistence. Proc. Natl. Acad. Sci. U.S.A 107:12541-12546.
47. Wang J D, Sanders G M, Grossman A D. 2007. Nutritional control of elongation of DNA replication by (p) ppGpp. Cell 128:865-875.
48. Fahlman R P, Dale T, Uhlenbeck O C. 2004. Uniform binding of aminoacylated transfer RNAs to the ribosomal A and P sites. Mol. Cell 16:799-805.
49. Haseltine W A, Block R. 1973. Synthesis of guanosine tetra- and pentaphosphate requires the presence of a codon-specific, uncharged transfer ribonucleic acid in the acceptor site of ribosomes. Proc. Natl. Acad. Sci. U.S.A 70:1564-1568.
50. Correia F F, D'Onofrio A, Rejtar T, Li L Y, Karger B L, Makarova K, Koonin E V, Lewis K. 2006. Kinase activity of overexpressed HipA is required for growth arrest and multidrug tolerance in *Escherichia coli*. J. Bacteriol. 188:8360-8367.
51. Cortay J C, Cozzone A J. 1983. Effects of aminoglycoside antibiotics on the coupling of protein and RNA syntheses in *Escherichia coli*. Biochem. Biophys. Res. Commun. 112:801-808.
52. Christensen S K, Gerdes K. 2004. Delayed-relaxed response explained by hyperactivation of RelE. Mol. Microbiol. 53:587-597.
53. Nguyen D, Joshi-Datar A, Lepine F, Bauerle E, Olakanmi O, Beer K, McKay G, Siehnel R, Schafhauser J, Wang Y, Britigan B E, Singh P K. 2011. Active starvation responses mediate antibiotic tolerance in biofilms and nutrient-limited bacteria. Science 334:982-986.
54. Kasari V, Mets T, Tenson T, Kaldalu N. 2013. Transcriptional cross-activation between toxin-antitoxin systems of *Escherichia coli*. BMC Microbiol. 13:45.10.1186/1471-2180-13-45
55. Suzuki M, Zhang J J, Liu M, Woychik N A, Inouye M. 2005. Single protein production in living cells facilitated by an mRNA interferase. Mol. Cell 18:253-261
56. Brown L, Gentry D, Elliott T, Cashel M. 2002. DksA affects ppGpp induction of RpoS at a translational level. J. Bacteriol. 184:4455-4465.
57. Zaslaver A, Bren A, Ronen M, Itzkovitz S, Kikoin I, Shavit S, Liebermeister W, Surette M G, Alon U. 2006. A comprehensive library of fluorescent transcriptional reporters for *Escherichia coli*. Nat. Methods 3:623-628.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

HipA-Triggered Growth Arrest and β-Lactam Tolerance in *Escherichia coli* are Mediated by RelA-Dependent ppGpp Synthesis Persistence is a phenomenon whereby a subpopulation of bacterial cells enters a transient growth-arrested state that confers antibiotic tolerance. While entrance into persistence has been linked to the activities of toxin proteins, the molecular mechanisms by which toxins induce growth arrest and the persistent state remain unclear. Here, we show that overexpression of the protein kinase HipA in *Escherichia coli* triggers growth arrest by activating synthesis of the alarmone guanosine tetraphosphate (ppGpp) by the enzyme RelA, a signal typically associated with amino acid starvation. We further demonstrate that chemically suppressing ppGpp synthesis with chloramphenicol relieves inhibition of DNA replication initiation and RNA synthesis in HipA-arrested cells and restores vulnerability to β-lactam antibiotics. HipA-arrested cells maintain glucose uptake and oxygen consumption and accumulate amino acids as a consequence of translational inhibition. We harness the active metabolism of HipA-arrested cells to provide a bacteriophage-resistant platform for the production of biotechnologically relevant compounds, which may represent an innovative solution to the costly problem of phage contamination in industrial fermentations.

We sought to determine if HipA expression triggers ppGpp synthesis and if ppGpp is directly responsible for the general attenuation of macromolecular synthesis and development of antibiotic tolerance. We also wished to examine some aspects of the metabolic response to HipA-mediated growth arrest, as recent reports indicate that persister cells maintain an active metabolism (20). We find that HipA expression activates ppGpp synthesis by the ribosome-associated ppGpp synthetase RelA, leading to inhibition of macromolecular synthesis, triggering growth arrest, and enabling resistance to β-lactam antibiotics. This establishes the mechanistic link between HipA expression and several major traits of persistence. We also found that HipA-arrested cells maintain metabolic activity and attenuate anabolism by feedback inhibition.

Materials and Methods

Strains, Media, and Plasmids.

Oligonucleotides used in this study are listed in Table 1. Plasmids and strains used in this study are listed in Table 2. *Escherichia coli* DH10B, grown in LB medium, was used for cloning and plasmid amplification. Unless otherwise noted, for all HipA arrest experiments we used morpholinepropanesulfonic acid (MOPS)-M9 medium with 0.4% glucose and $NH_4Cl$ supplemented to 2 g/liter, with 50 µg/ml kanamycin added when appropriate. *E. coli* MG1655 (ATCC) was used for all persistence experiments. Experiments to determine the involvement of RelA in growth arrest were performed using *E. coli* strains CF1648 (MG1655, here referred to as the WT [wild type] strain) and CF12510 (MG1655, here referred to as the ΔrelA strain), which were generously provided by Michael Cashel. hipA was cloned from MG1655 genomic DNA using the primers GB081210-hipA-BB.F and GB081210-hipA-BB.R. The PCR fragment was digested using BglII and XhoI enzymes and ligated into BglII-XhoI-digested BglBrick plasmid pBbS2k to make pHipA. For measurement of HipA expression and ppGpp timing, an operon containing both hipA and gfpmut2 genes was constructed. Green fluorescent protein (GFP) was amplified from pUA66 using primers GB042111-GFPmut2.f and GB042111-GFPmut2.r, and the PCR product was digested with BglII and XhoI and ligated into pHipA digested with BamHI and XhoI, creating pHipA-GFP. Plasmid pBbA5c-MTSA, carrying genes atoB (codon optimized for *E. coli* [21]), *Staphylococcus aureus* mvaA, and *S. aureus* mvaS (22) encoding a heterologous mevalonate pathway, was assembled on the pBbA5c backbone using standard BglBrick cloning procedures (23). atoB was amplified from the pBbA5c-MevT-MBIS (fixed) plasmid using primers atoB-fw and atoB-rw. mvaA was amplified from plasmid pTSAmvaASP using primers mvaA_fw and mvaA_rv. mvaS was amplified in two PCRs using primer pair mvaS_fw and EcoRIdel_Rv and primer pair EcoRIdel_Fw and mvaS_rv in order to remove an internal EcoRI restriction site, and the results were linked by splice-by-overlap extension (SOE) PCR (24) using primers mvaS_fw and mvaS_rv.

TABLE 1

Oligonucleotides used in this study.

| Oligonucleotide | Sequence (5'-3') |
|---|---|
| GB081210-hipA-BB.F | TTC AAA AGA TCT CAA CAG AAC AGC AAA ATC TGG AGT GG (SEQ ID NO: 2) |
| GB081210-hipA-BB.R | TCC TTA CTC GAG TTA GGA TCC TCA CTT ACT ACC GTA TTC TCG GCT TAA C (SEQ ID NO: 3) |
| GB042111-GFPmut2.f | TTA TCC AGA TCT AGG AGG AAA AAA AAA TGA GTA AAG GAG AAG AAC TTT TCA CTG G (SEQ ID NO: 4) |
| GB042111-GFPmut2.r | ATA CCA CTC GAG TTT GGA TCC TTA TTT GTA CAA TTC ATC CAT ACC ATG GGT AAT C (SEQ ID NO: 5) |
| AtoB-fw | GAA TTC AAA AGA TCT AGA GAA TAT A (SEQ ID NO: 6) |
| AtoB-rv | CTC GAG TTT GGA TCC TCA ATT CAA CCG TTC AAT (SEQ ID NO: 7) |
| mvaA_fw | GAA TTC AAA AGA TCT ATT CAG GAA ACA GAC CAT GTC CAT GCA A (SEQ ID NO: 8) |
| mvaA_rv | CTC GAG TTT GGA TCC TTA TTG TTG TCT AAT (SEQ ID NO: 9) |
| mvaS_fw | GAA TTC AAA AGA TCT AGG AGA AAC TTA ATG (SEQ ID NO: 10) |
| mvaS_rv | CTC GAG TTT GGA TCC TTA CTC TGG TCT GTG AT (SEQ ID NO: 11) |
| EcoRIdel_Fw | TGG ATT GAA CTC AGG CGG CGA GC (SEQ ID NO: 12) |
| EcoRIdel_Rv | GCT CGC CGC CTG AGT TCA ATC CAT AAC GTG CT (SEQ ID NO: 13) |

TABLE 2

Plasmids and strains used in this study.

| Strain or plasmid | Description | Reference or source |
|---|---|---|
| Strain | | |
| *Escherichia coli* DH10B | *E coli* strain for cloning and plasmid amplification | Invitrogen |
| *Escherichia coli* MG1655 | *E coli* strain for growth arrest and antibiotic resistance studies | ATCC |
| *Escherichia coli* CF1648 (MG1655) | *E coli* strain MG1655 for direct comparison with ΔrelA strain | 56; Michael Cashel, National Institues of Health |
| *Escherichia coli* CF12510 (MG1655 ΔrelA) | *E coli* strain Mg1655 relA256 (unmarked) | 56, Michael Cashel, National Institues of Health |
| Plasmids | | |
| pHipA | HipA underthe control of $P_{tet}$ promoter | This work |
| pHipA-GFP | HipA GPPmut2 transcriptional fusion | This work |
| pUA66 | Source of gfpmut2 gene | 57 |
| pBb52k | Plasmid backbone for pHipA | 23 |
| pBbA5c-MTSA | Encodes mevalonate pathway | This work |
| pBbA5c-Mevt-MB15(fixed) | Source of codon-optimized atoB | 21 |
| pTSAmvaASP | Source of *S. aureus* munS and munA genes | S. W. Kim, Kyunsang National University, South Korea | ppGpp measurements performed with high-performance liquid chromatography (HPLC).

ppGpp and nucleotides were extracted from cells grown on agar-supported nylon filters, following a protocol inspired by the rapid-quenching and metabolite extraction approach described in reference 25. We adopted this technique to avoid perturbing ppGpp levels with lengthy cell harvesting and extraction procedures, as the enzymes that generate and degrade ppGpp are known to respond rapidly to external conditions (26). Briefly, cells grown in liquid medium to an optical density at 600 nm ($OD_{600}$) of ~0.1 were transferred to nylon filters and adhered to solid agar plates containing our modified MOPS-M9 medium. Persistence was induced when filter-supported cells reached an $OD_{600}$ of 0.5 by transferring the filters to agar plates containing the same medium supplemented with 50 ng/ml anhydrous tetracycline (aTc). To induce rapid growth arrest by isoleucine starvation, filters were transferred to solid medium containing 40 µg/ml valine. Metabolism was rapidly quenched by transferring the filters into 5 ml of 2 M ice-cold formic acid for 30 min, after which the solutions were collected and neutralized by the use of 1 ml of 15% ammonium bicarbonate, flash-frozen in liquid nitrogen, and lyophilized. Lyophilized cells were resuspended in 0.2 ml cold 50% methanol, centrifuged again to precipitate insoluble debris, and spin filtered using a Amicon UFC500396 centrifugal filter unit (molecular weight cutoff [MWCO] of 3) in a refrigerated centrifuge set to −2° C. to remove soluble proteins. Concentrations of ppGpp and GTP were measured using anion-exchange chromatography and a Partisil 5 Sax Rac II column (catalog no. 422-227; Hichrom Limited), with a silica Nova-Pak guard column (catalog no. WAT046845; Whatman) per a protocol described previously (26) and modified for brevity. Buffers A and B consisted of 0.05 M and 1 M ammonium phosphate (pH 3.4), respectively. Filtered extracts (25 µl) were injected, and the mobile phase was ramped to a buffer B level of 100% over 4 min and a flow rate of 1 ml/min. At 4.5 min, the rate was increased to 1.5 ml/min and the process was run until 10 min, at which point the mobile phase was ramped back down to 0% buffer B and was run through the column for 20 min. The column temperature was maintained at 50° C., and absorbance was monitored at 254 nm. The ppGpp standard was purchased from Trilink Biotechnologies (N-6001).

For measurements of hipA expression using the hipA-gfpmut2 transcriptional fusion, GFP measurements were made in parallel with ppGpp measurements, which were performed as described above using MG1655/pHipA-GFP cells. To measure GFP, translation was quenched by transferring filters to 5 ml of $H_2O$ with 30 µg/ml chloramphenicol. GFP fluorescence measurements were performed 30 min after translational quenching to enable translated GFP to become fluorescent. GFP fluorescence (excitation, 488 nm; emission, 510 nm) was measured using a Spectromax M2 reader (Molecular Devices).

Measurement of DNA and RNA Concentrations.

Cultures of MG1655/pHipA cells were inoculated into 40 ml of MOPS-M9 medium in 250-ml unbaffled Erlenmeyer flasks and incubated with shaking at 37° C. When the $OD_{600}$ reached ~0.3, aTc was added to reach 50 ng/ml. After 1 h of HipA induction, a sample was removed for DNA or RNA extraction, the cultures were split into two 15-ml cultures, and 30 µg/ml chloramphenicol was added to one of the cultures. For comparison of DNA and RNA synthesis results in WT and ΔrelA strains expressing HipA, biological triplicates of the WT/pHipA and ΔrelA/pHipA strains were grown in MOPS-M9 medium at 37° C. to an $OD_{600}$ of 0.2 to 0.4, at which point HipA expression was induced by addition of aTc to 50 ng/ml. Samples were processed per a previously published protocol (27) using Picogreen (Invitrogen) for DNA quantification. RNA was quantified by measurement of fluorescence using the Quant-It assay (catalog no. Q33140; Invitrogen) following the manufacturer's instructions. Fluorescence was measured using a Spectromax M2 reader.

β-Lactam Susceptibility of HipA-Arrested Cells.

Biological triplicates of MG1655/pHipA cells were inoculated into 30 ml of MOPS-M9 medium and grown at 37° C. until an $OD_{600}$ of 0.5 was reached. aTc was added to reach 50 ng/ml, and the cultures were split into two 12-ml subcultures. At 2.5 h later, carbenicillin (100 µg/ml) was added to one subculture and optical densities were measured. For comparison of the levels of β-lactam tolerance of WT and ΔrelA cultures expressing HipA, biological triplicates of the WT/pHipA and ΔrelA/pHipA strains were inoculated into 5 ml of MOPS-M9 medium and grown at 37° C. HipA expression was induced with 50 ng/ml aTc when the $OD_{600}$ reached ~0.3. Ampicillin was added to reach a final concentration of 100 µg/ml 1.5 h later, and optical densities were monitored.

Measurement of Glucose Consumption and Respiration.

Cultures were incubated in a Respiration Activity MOnitoring System (RAMOS; HiTec Zang) at 37° C. in Erlenmeyer flasks with shaking in a Lab Therm LT-X incubator (Kuhner) (28). Overnight cultures of the MG1655/pHipA strain were inoculated at 1/100 into 20 ml of pre-equilibrated MOPS-M9 glucose medium. Samples were periodically removed for glucose concentration and growth measurements. Glucose concentrations were quantified via HPLC, using an Aminex HPX-87H column maintained at 50° C. while running 4 mM $H_2SO_4$ at a constant rate (0.6 ml/min) on an Agilent 1200 system equipped with a refractive index detector.

Metabolite Concentration Measurements.

Intracellular metabolites were measured using an isotopic ratio-based approach, largely as described previously (25), with slight modifications. Briefly, cells were grown on agar plates with our modified MOPS-M9 medium with 0.4% glucose fully labeled with $^{13}C$ (CLM-1396; Cambridge Isotope Laboratories). Cells were grown in liquid medium and transferred to nylon filters, and the nylon filters were adhered to solid medium as described above. Persistence was induced by transferring filters to agar plates containing 50 ng/ml aTc, and metabolism was rapidly quenched by transferring the filter to a petri dish containing 40:40:20 acetonitrile:methanol:water (with 0.1 M formic acid) and isotopically unlabeled metabolite standards. After 30 min of quenching, the extract was used to wash cellular debris from the filters and collected into a Falcon tube. An additional 2.5 ml of quenching solution (without metabolite standards) was used to wash the filter and the petri dish once more and collected into the same Falcon tube. Finally, 0.5 ml of 15% ammonium bicarbonate was added to the extract to neutralize the solution, and the solution was flash-frozen in liquid nitrogen and lyophilized. Lyophilized samples were resuspended in 200 µl of 50% methanol and filtered as with the ppGpp extracts (described above), and the filtered extract was analyzed using tandem liquid chromatography/mass spectroscopy (LC/MS). LC/MS protocols for measuring nucleotide, organic acids, and sugar phosphate concentrations were used as previously described (29).

For measurement of intracellular amino acids, liquid chromatographic separation was conducted at 30° C. with a Kinetex hydrophilic interaction LC (HILIC) column (Phenomenex, Torrance, Calif.) (100-mm length, 4.6-mm internal diameter, 2.6-µm particle size) using a 1200 Series HPLC system (Agilent Technologies, Santa Clara, Calif.). The injection volume for each measurement was 2 µl. The mobile phase was composed of 20 mM ammonium acetate-water (solvent A) and 10 mM ammonium acetate-90% acetonitrile-10% water (solvent B) (HPLC grade; Honeywell Burdick & Jackson). Ammonium acetate was prepared from a stock solution of 100 mM ammonium acetate and 0.7% formic acid (Sigma-Aldrich, St. Louis, Mo.) (98% to 100% chemical purity) in water. Amino acids were separated with the following gradient: 90% to 70% solvent B for 4 min followed by a hold at 70% solvent B for 1.5 min, 70% to 40% solvent B for 0.5 min followed by a hold at 40% solvent B for 5.5 min, and 40% to 90% solvent B for 0.5 min followed by a hold at 90% solvent B for 2 min. The flow rate was adjusted as follows: 0.6 ml/min for 12.5 min and 0.6 ml/min to 1 ml/min for 0.5 min followed by a hold at 1 ml/min for 2 min.

The HPLC system was coupled to an Agilent Technologies 6210 time-of-flight mass spectrometer (TOF MS) with a 1:6 postcolumn split. Nitrogen gas was used as both the nebulizing gas and the drying gas to facilitate the production of gas-phase ions. The drying and nebulizing gases were set to 12 liters/min and 25 lb/in$^2$, respectively, and a drying gas temperature of 320° C. was used throughout. Fragmentor, skimmer, and optical coherence tomography 1 (OCT1) radio frequency (RF) voltages were set to 100 V, 50 V, and 170 V, respectively. Electrospray ionization (ESI) was conducted in the positive-ion mode with a capillary voltage of 3.5 kV. MS experiments were carried out in the full-scan mode (m/z 70 to 340) at 0.86 spectra per second for the detection of [M+H]$^+$ ions. The instrument was tuned for a range of m/z 50 to 1,700. Prior to LC-ESI-TOF MS analysis, the TOF MS was calibrated with the Agilent ESI-Low TOF tuning mix.

The separation of nucleotides was conducted on a ZIC-pHILIC column (Merck SeQuant [distributed via The Nest Group, Inc., Southborough, Mass.) (150-mm length, 2.1-mm internal diameter, and 5-µm particle size) using an Agilent Technologies 1200 Series HPLC system. Injection volumes for the measurement of chemical standards and metabolites from biological extracts were 2 and 4 µl, respectively. The column compartment was set to 30° C. All other chromatographic conditions were as described above. The mobile phase was composed of (A) 100 mM ammonium carbonate in water and (B) acetonitrile. A flow rate of 0.23 ml/min was used unless otherwise stated. Nucleotide separation was conducted as follows: 78% B (0 min), 48% B (17 min), 78% B (20 min), 78% B (20.5 min), and 78% B (25 min). The flow rate was increased from 0.23 to 0.3 ml/min from 20 to 20.5 min and held for a further 4.5 min. The HPLC system was coupled to TOF MS with a 1:3 postcolumn split. ESI was conducted in the negative ion mode, and a capillary voltage of 3.5 kV was utilized. Fragmentor, skimmer, and OCT1 RF voltages were set to 200 V, 65 V, and 300 V, respectively. MS experiments were carried out in the full-scan mode (m/z 335 to 810). All other MS conditions were as described above. The LC/MS protocol for measuring pyruvate concentrations was taken from reference 30.

Kinetic Flux Measurements.

Flux through amino acid pools was measured using kinetic flux profiling as described in reference 31. Briefly, filter-grown cells induced into the persistent state were transferred to solid medium containing medium with aTc and 0.4% $^{13}$C-labeled glucose. At set times, filters were removed and quenched as described above for the metabolite concentration measurements. Ratios of unlabeled metabolites to metabolites labeled at any position were determined for each time point as described above.

For determining flux for each metabolite, an upstream precursor metabolite was found and its replacement rate was determined. This rate was used as a fixed parameter in a subsequent fitted equation for the amino acid as described previously (31). Suitable precursor metabolites could not be found for all amino acids (e.g., shikimate for the aromatic amino acids) because of instability of the precursor under our extraction conditions. Amino acids and the corresponding precursors used are listed in Table 3.

TABLE 3

Amino acids and their precursors used for kinetic flux profiling.

| Amino acid | Precursor metabolite |
|---|---|
| Alanine | Pyruvate |
| Threonine | Aspartic acid |
| Methionine | Aspartic acid |
| Proline | Glutamate |
| Arginine | Glutamate |
| Asparagine | Aspartic acid |
| Lysine | Pyruvate |
| Isoleucine | Pyruvate |
| Glutamine | Glutamate |

Antibiotic Resistance.

Persister cells were prepared in triplicate by ofloxacin treatment of stationary-phase cultures based on a previously described protocol (32). Overnight cultures of MG1655 cells grown in LB medium for 20 h were treated with ofloxacin for 3 h at 37° C., after which cells were pelleted, washed with fresh LB medium, pelleted again, and resuspended in antibiotic-free LB medium. After resuspension, chloramphenicol (30 µg/ml) and ampicillin (100 µg/ml) were added singly or in combination, and cells were incubated at 37° C. with shaking for 4 h. Samples were removed, pelleted once, washed with LB medium, resuspended, and serially diluted. A 10-µl volume of the serial dilutions was spot plated on an LB agar plate, which was incubated at 37° C. overnight. Colonies were counted the following day.

Mevalonate Production.

MG1655/pHipA cells were transformed with pBbA5c-MTSA. Overnight cultures were inoculated at 1/50 into 50 ml modified MOPS-M9 medium (Teknova) with 1% glucose, 50 µg/ml kanamycin, 30 µg/ml chloramphenicol, and 1 µg/ml nystatin and grown at 30° C. At an OD of 0.18, isopropyl-β-d-thiogalactopyranoside (IPTG) was added to the cultures to induce expression of the mevalonate pathway. At 5 h later (OD of ~0.8), 100 ng/ml aTc was added to induce persistence, and 3 h later carbenicillin was added to reach 50 µg/ml to prevent the growth of cells that resisted HipA-induced arrest. Additional medium was added after 35 and 82 h to sustain mevalonate production with fresh glucose. At 99 h, nystatin was added to the cultures (final concentration, 100 µg/ml) to prevent mold growth. For measurement of extracellular mevalonate, culture samples were removed and the cells were pelleted by centrifugation. The supernatant was transferred to an equal volume of ice-cold methanol, and the mixture was spin filtered as described above. Mevalonate was measured using an LC-MS method for organic acids (29).

Phage Resistance.

Overnight cultures of MG1655/pHipA/pBbA5c-MTSA cells were inoculated at 1/50 into 50 ml medium (as described for mevalonate production) plus 10 mM MgSO$_4$ and 5 mM CaCl$_2$ to enable phage binding and lysis and were grown with shaking at 30° C. At an $OD_{600}$ of ~0.2, IPTG was added to reach a final concentration of 250 µM. At 5 h later (OD of ~0.8), the cultures were split into two 25-ml subcultures, and aTc was added to 100 ng/ml to one of the subcultures. At 4 h later, carbenicillin (100 µg/ml) was added to the aTc-induced cultures to prevent growth of mutants that resisted growth arrest, and the cultures were further split into 5-ml tubes. At this time, 1 µl of a chloroform-sterilized P1vir lysate was added to the appropriate tubes. At 17 h later, all cultures were subcultured at 1/20 into 5 ml of fresh medium with additives identical to those used with the parent tubes. Samples were removed, cells and cell debris were pelleted, the supernatant was removed and spin filtered, and mevalonate in the filtrate was measured as before.

Results

HipA Expression Causes Growth Arrest and ppGpp Biosynthesis by RelA.

Figure 7:
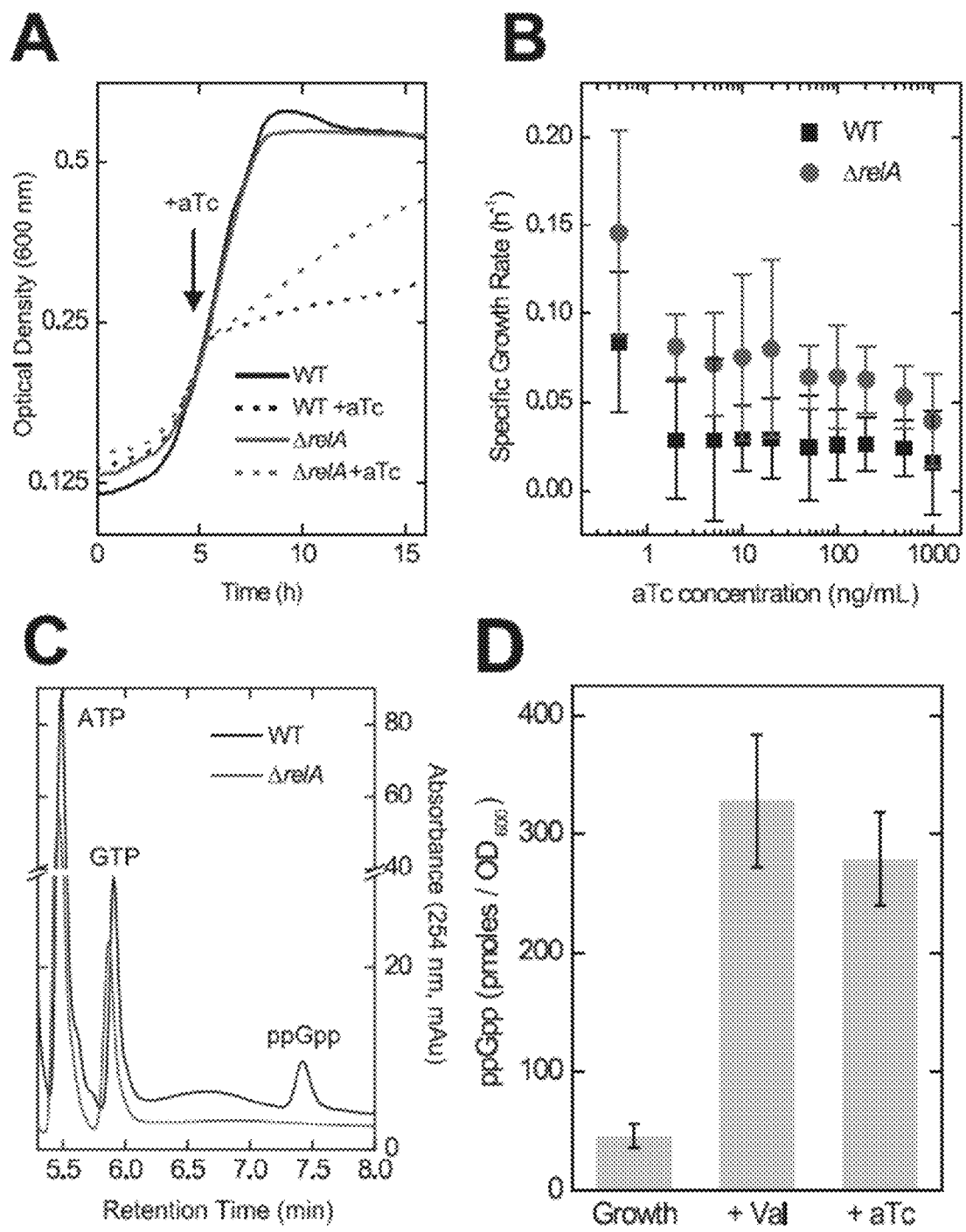
FIG. 7 shows that HipA expression activates ppGpp synthesis by the enzyme RelA, which is required for complete growth arrest and the persistent state. (A) Growth curves of WT and ΔrelA *E. coli* MG1655 (solid black and red, respectively) bearing the plasmid pHipA. At the indicated time, 50 ng/ml anhydrous tetracycline (aTc) was added to the cultures, inducing growth arrest after ~45 min (dotted lines). (B) Specific growth rates of WT and ΔrelA strains measured 1 h after addition of various amounts of aTc. Error bars represent averages of at least 32 data point pairs. (C) Representative chromatogram of nucleotide extract of WT and ΔrelA plate-grown cultures after 90 min of HipA induction. mAu, milliabsorbance units. (D) ppGpp concentration measured in cells during exponential growth, cells starved for isoleucine by the addition of valine (+Val), and cells experiencing HipA-mediated growth arrest (+aTc). Error bars represent the standard deviations of the results of at least three measurements. (E) Timing of ppGpp synthesis in response to HipA expression and growth arrest. A hipA-gfpmut2 operon enabled HipA expression to be indirectly monitored with GFP fluorescence.
Figure 7:
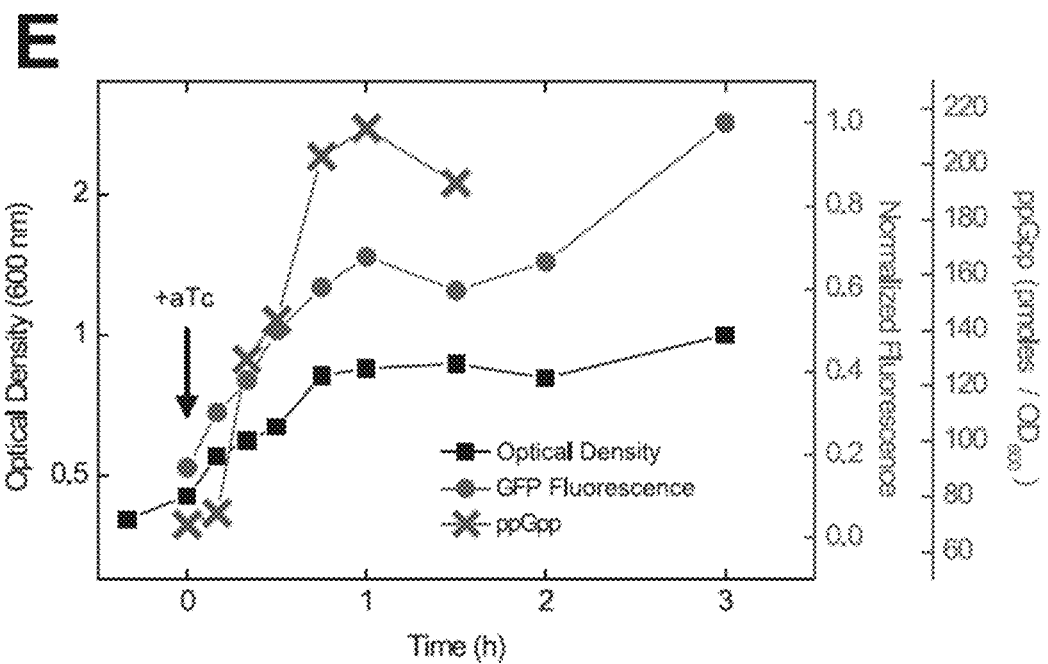

We introduced plasmid pHipA, a low-copy-number plasmid carrying hipA under the control of a tetracycline-inducible promoter ($P_{Tet}$), into an E. coli MG1655 derivative (CF1648, here referred to as the WT strain) and a relA-knockout MG1655 strain (CF12510, here referred to as the ΔrelA strain). HipA expression was induced during exponential growth with anhydrous tetracycline (aTc), causing nearly complete growth arrest in the WT strain. In contrast, HipA expression in the ΔrelA strain sharply inhibited growth but did not arrest growth completely (FIG. 7A). Increasing the concentration of the chemical inducer aTc did not suppress the residual growth observed in the ΔrelA strain, as the specific growth rates after HipA induction did not significantly change at concentrations above 2 ng/ml aTc (FIG. 7B; average growth rates, 0.025±0.010 $h^{-1}$ for the WT strain and 0.066±0.012 $h^{-1}$ for the ΔrelA strain).

The residual growth observed in the ΔrelA strain during HipA expression suggests that growth arrest by HipA requires ppGpp synthesis by RelA. To determine if ppGpp is produced by RelA in HipA-expressing cells, we measured ppGpp concentrations 1.5 h after HipA induction in both WT and ΔrelA strains. HipA expression triggered ppGpp biosynthesis in WT cells but not in ΔrelA cells (FIG. 7C). ppGpp concentrations in HipA-arrested WT cells approached the levels measured in cells starved for an amino acid (FIG. 7D). In order to establish the timing of ppGpp synthesis relative to HipA expression, we constructed a transcriptional fusion of hipA and gfpmut2 by inserting a gfpmut2 gene immediately after hipA in a single operon. We found that ppGpp was synthesized quickly after hipA induction and reached its maximum concentration once growth arrest had completed (FIG. 7E).

HipA Activity does not Induce ppGpp Biosynthesis by Causing Amino Acid Starvation.

Figure 8:
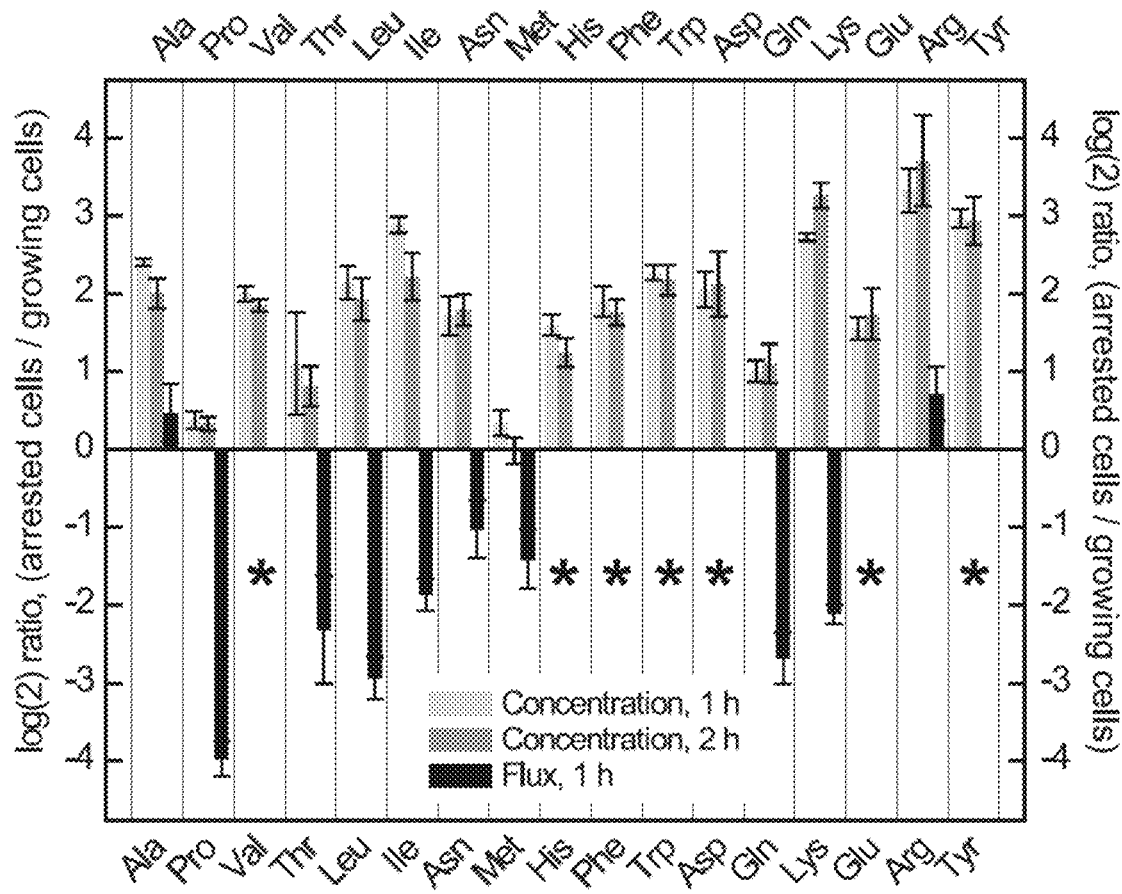
FIG. 8 shows that growth arrest by HipA induction causes intracellular accumulation of amino acids, indicating that HipA does not trigger ppGpp synthesis by causing amino acid depletion. Light gray and dark gray bars represent $\log_2$ amino acid concentration ratios of HipA-arrested cells to growing cells, as measured in cells 1 and 2 h after HipA induction by addition of aTc. Black bars indicate ratios (HipA-arrested cells/growing cells) of flux through indicated amino acid pools determined using kinetic flux profiling. A value of 0 indicates no change. For concentration measurements, error bars represent the standard deviations of the results of three biological replicates. Error bars in flux bars represent uncertainty in flux determination, as described in Materials and Methods. Asterisks indicate amino acid fluxes for which values could not be determined.

Because ppGpp synthesis by RelA can be triggered by amino acid starvation, we asked whether HipA expression somehow increases ppGpp by causing a reduction in amino acid concentrations. We measured the intracellular concentrations of amino acids 1 h after induction of hipA expression (approximately 15 min after growth arrest). We found that most amino acid concentrations were elevated several-fold over those measured in actively growing cells (FIG. 8, light gray and dark gray bars) and did not significantly change after 1 h of growth arrest, indicating that HipA expression does not trigger ppGpp levels by inducing starvation. We attribute the increase in amino acid levels to the decreased translational activity of HipA-arrested cells.

Translation Inhibition Likely Attenuates Amino Acid Biogenesis.

To understand how HipA-arrested cells might regulate anabolism in the absence of growth, we used kinetic flux profiling (31) to determine if the increase in amino acid concentrations would suppress their biosynthesis. Briefly, filter-supported cells were quickly transferred from solid medium containing unlabeled glucose to medium containing isotopically labeled glucose, and the washout rate of unlabeled metabolites was determined in both growing cells and HipA-arrested cells. We confirmed that flux through several of the amino acid pools was dramatically reduced (FIG. 8, black bars), which we suspect was a result of feedback inhibition exerted directly by accumulated amino acids upon their respective biosynthetic pathways.

ppGpp Inhibits DNA and RNA Biosynthesis in HipA-Arrested Cells.

Having established that HipA expression triggers the production of ppGpp via RelA activation, we next sought to confirm that ppGpp inhibits DNA and RNA synthesis in HipA-arrested cells. Chloramphenicol, a bacteriostatic drug that inhibits translation, is also known to suppress ppGpp levels in cells starved for amino acids (33). We found that chloramphenicol treatment caused the ppGpp concentration within HipA-arrested cells to decrease by 60% (±20%) within 15 min. Chloramphenicol treatment relieved inhibition of both DNA synthesis and RNA synthesis (FIGS. 9A and 9B), indicating that ppGpp blocks DNA and RNA synthesis within HipA-arrested cells. Furthermore, HipA expression was not able to inhibit RNA synthesis in the ΔrelA strain, as RNA concentrations continued to increase for over 2 h after growth arrest (Table 4).

TABLE 4

DNA/OD and RNA/OD ratios observed after HipA arrest (1 h after addition of aTc) in WT and ΔrelA strains, normalized to ratio determined at 1 h after addition of aTc.

| Ratio for indicated strain | Avg ratio to value at 1 h after HipA induction | SD |
|---|---|---|
| DNA/OD (6 h after arrest) | | |
| WT | 1.05 | 0.02 |
| ΔrelA | 1.09 | 0.02 |
| RNA/OD (2 h after arrest) | | |
| WT | 0.99 | 0.02 |
| ΔrelA | 1.54 | 0.15 |

We observed only slight increases in intracellular DNA concentrations in both WT and ΔrelA cultures over 6 h after HipA arrest (Table 4). Similar results have been observed in wild-type (WT) and ΔrelA strains subjected to translation inhibition by treatment with an amino acid analog (34), indicating that non-antibiotic-induced translational inhibition also contributes to regulation of DNA replication, as discussed below.

ppGpp Provides Resistance to β-Lactam Antibiotics in HipA-Arrested Cells.

Figure 9:
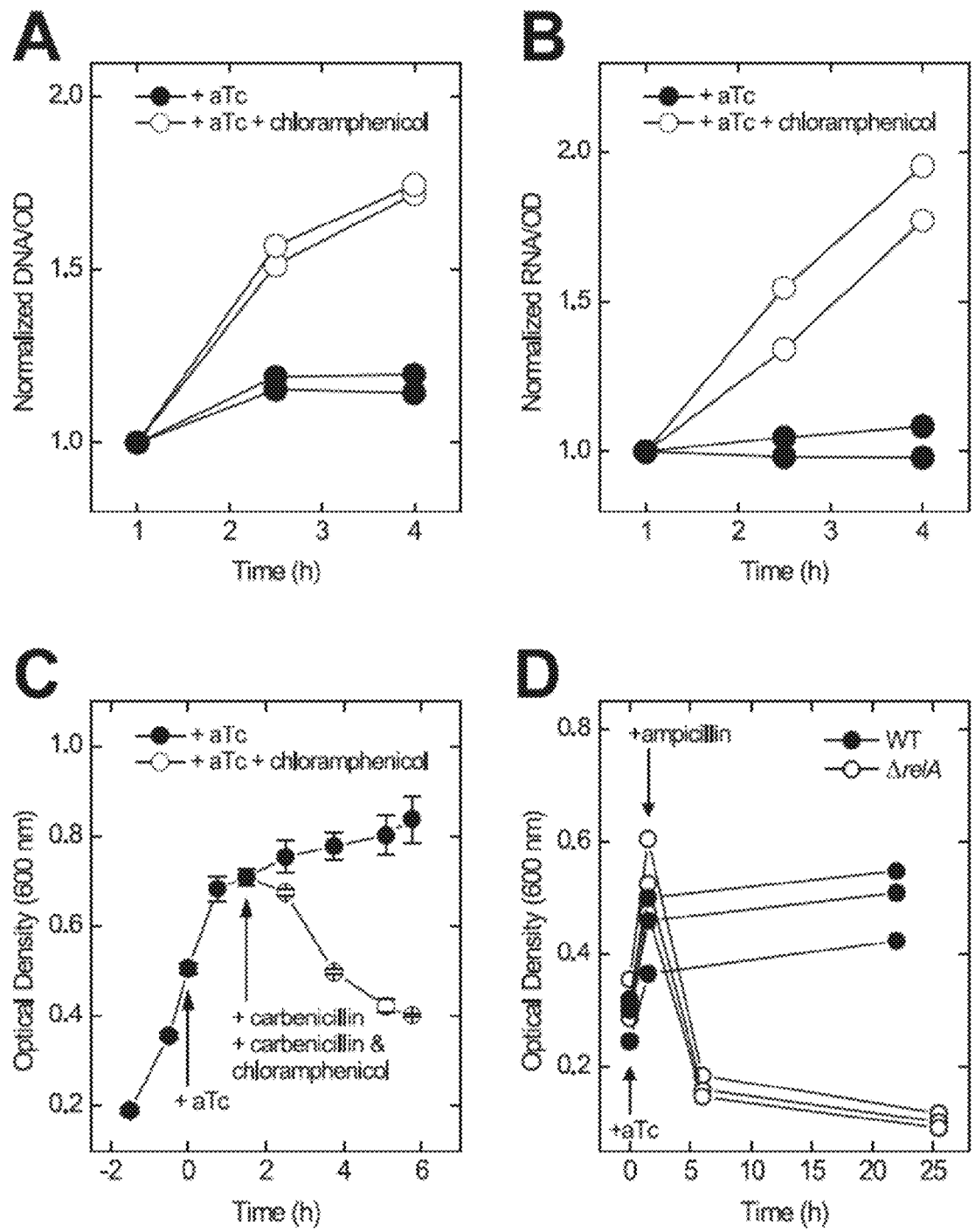
FIG. 9 shows that RelA-dependent synthesis of ppGpp is responsible for the inhibition of macromolecular synthesis observed in HipA-arrested cells. (A and B) Chloramphenicol relieves the inhibition of DNA replication initiation (A) and RNA synthesis (B) imposed by ppGpp. DNA/OD and RNA/OD values were normalized to the value at 1 h. Data represent the results of biological duplicates. (C) Deactivation of ppGpp synthesis by chloramphenicol resensitizes HipA-arrested cells to β-lactam antibiotics. Carbenicillin (100 µg/ml) was added to all cultures at the time indicated. Error bars represent standard deviations of the results of biological triplicates. (D) HipA expression does not enable ΔrelA cells to resist ampicillin (added to 100 µg/ml). Shown are the results of biological triplicates.

The induction of ppGpp synthesis by toxins may also provide the mechanistic basis for the tolerance of β-lactam antibiotics by some persister cells, as high ppGpp concentrations protect cells from lysis by β-lactams during amino acid starvation (35, 36) via inhibition of phospholipid biosynthesis (12). If ppGpp also protects HipA-arrested cells from β-lactams, deactivating ppGpp synthesis with chloramphenicol should sensitize the cells to β-lactam antibiotics, and HipA expression should not provide resistance against β-lactams in a ΔrelA strain. We found that adding the β-lactam carbenicillin alone did not induce lysis in HipA-arrested WT cells, confirming the protective nature of the HipA-arrested state (37). However, the addition of carbenicillin in combination with chloramphenicol triggered lysis (FIG. 9C), and expression of HipA did not confer ampicillin resistance to the ΔrelA strain (FIG. 9D).

Chloramphenicol Treatment of Naturally Occurring Persister Cells does not Increase Killing by β-Lactam Antibiotics.

Our finding that combining chloramphenicol with β-lactam treatment results in killing of HipA-arrested cells suggests that therapeutic interventions that deactivate ppGpp synthesis (or accelerate ppGpp hydrolysis) could render persistent infections readily treatable by antibiotics. We tested this possibility by first isolating naturally occurring persister cells by treating overnight cultures with the fluoroquinolone antibiotic ofloxacin for 4 h and subsequently subculturing the cells in fresh medium containing chloramphenicol, ampicillin, or both compounds. We found that chloramphenicol-ampicillin combination treatment did not significantly increase the killing rate of isolated persisters compared to ampicillin alone (28%±14% reduction in CFU by combination treatment compared to 41%±13% with ampicillin alone [P=0.3, unpaired t test]).

HipA-Arrested Cells Consume Glucose and Oxygen and Maintain High ATP Levels.

Figure 10:
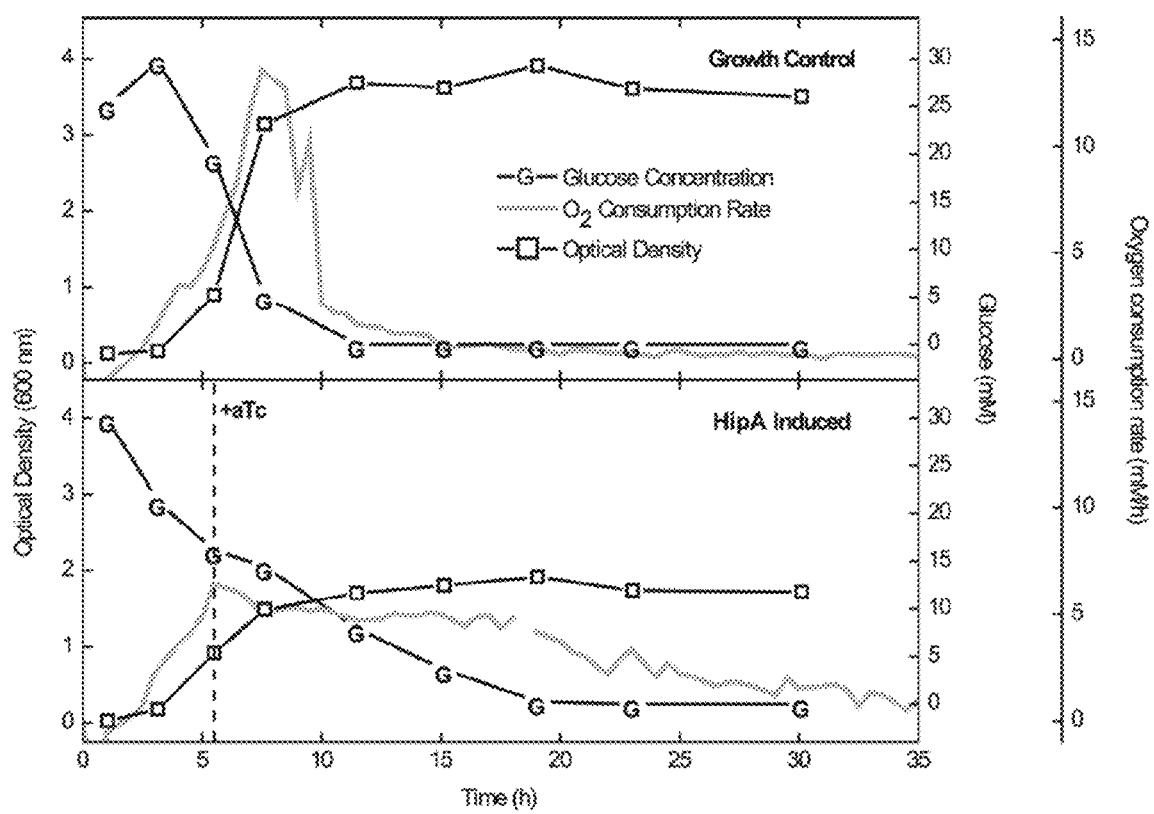
FIG. 10 shows that HipA-arrested cells maintain consume glucose and oxygen. Data represent glucose and oxygen consumption by a growing culture (top) and a HipA-arrested culture (bottom). At the indicated time (vertical dashed line), HipA expression was induced by the addition of aTc. Examples shown are representative of the results of three biological replicates.

We considered the alternative possibility that HipA enables tolerance by depleting ATP levels, which might also be expected to inhibit macromolecular synthesis. We found that the ATP charge was not significantly affected by HipA arrest (Table 5), suggesting to us that the cells maintain active respiration, as has been observed in naturally isolated persister cells (20). We measured glucose and oxygen consumption by cultures expressing hipA during exponential growth in glucose medium. As might be expected from our observations of high ATP concentrations, the HipA-arrested cultures continued to consume glucose and oxygen during growth arrest (FIG. 10), indicating that HipA-arrested cells maintain an active metabolism despite their lack of macromolecular synthesis.

TABLE 5

ATP charge of cells during growth and after HipA induction.

| Cell status | Avg ATP charge value$^a$ | SD |
| --- | --- | --- |
| Preinduction | 0.93 | 0.02 |
| HipA uninduced, 1 h | 0.90 | 0.02 |
| HipA induced, 1 h | 0.91 | 0.01 |

$^a$Data were calculated as follows: ([ATP] + 0.5 · [ADF])/([ATP] + [ADP] + [AMP]).

HipA-Arrested Cells can Maintain Production of Chemicals Via Synthetic Pathways and are Refractory to Phage Infection.

Having found that HipA-arrested cells are fully metabolically active, we next sought to exploit the active carbon flux within HipA-arrested cells to produce useful compounds via synthetic pathways. One advantage of using growth-arrested bacteria as a platform for the production of chemicals might be their higher resistance to phage-induced lysis compared with that of growing cells (38). Industrial-scale fermentations are extremely vulnerable to contamination by phage, which often causes considerable production losses. Prophylactic measures to prevent phage infection are costly and rarely completely effective, and decontamination often requires drastic measures, including shutdown of the affected plants (39-41). Technology to address the threat from phage could potentially relieve some of the need for these measures and decrease fermentation costs (42).

Figure 11:
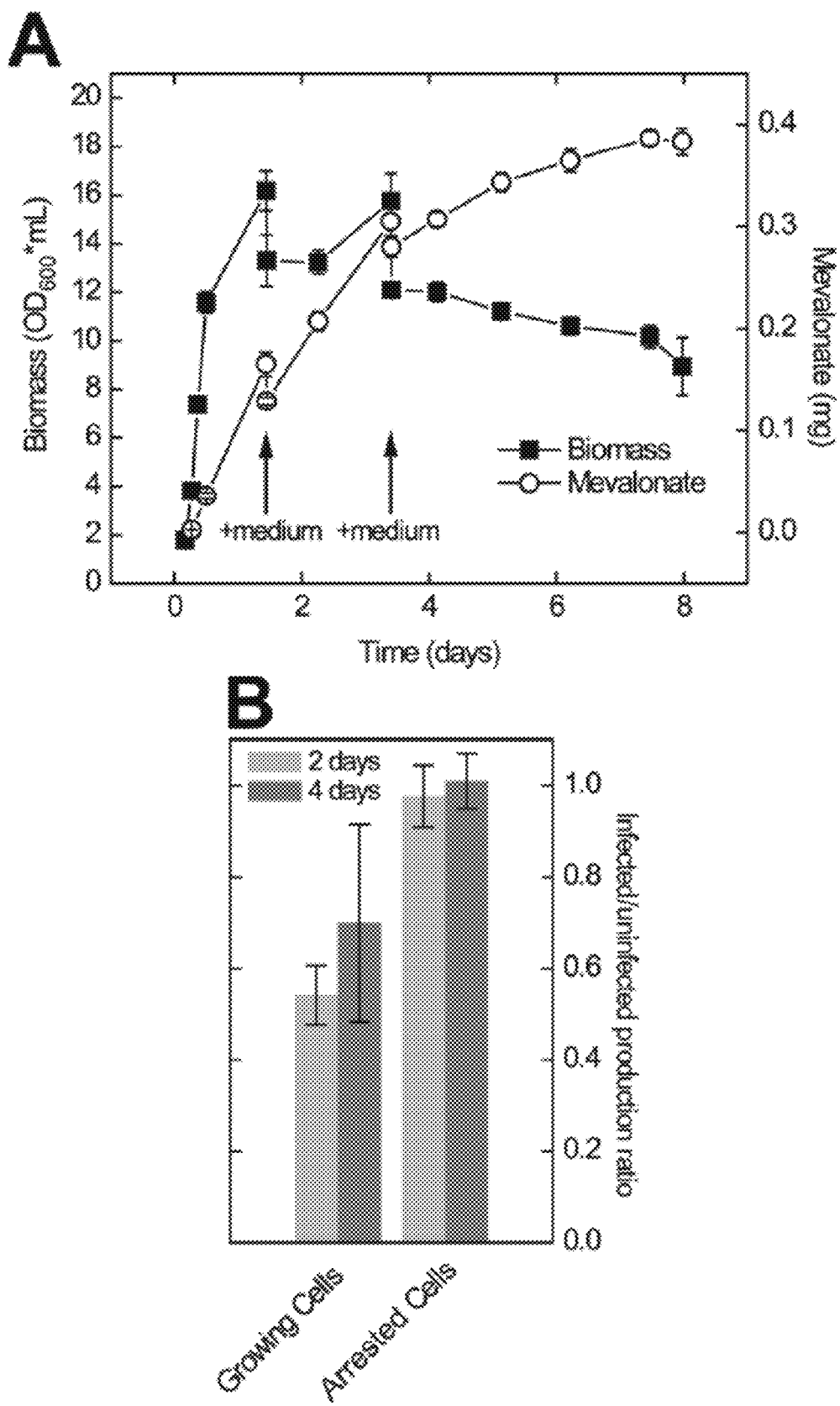
FIG. 11 show that HipA-arrested cells can maintain a heterologous pathway that enables production of mevalonate and are unaffected by infection by phage. (A) Production of mevalonate by HipA-arrested cells. A plasmid-encoded mevalonate pathway was induced with IPTG (at 0.17 days), and cells were subjected to growth arrest by HipA induction 5 h later (0.36 days). At the times indicated with arrows, fresh medium was added to the culture to replenish the supply of glucose for further production. (B) Production of mevalonate in HipA-arrested cells is unaffected by phage infection. Data represent mevalonate titers of phage-infected cultures expressed as ratios to titers obtained from uninfected cultures.

As a proof of concept, we sought to determine if HipA-arrested cells could produce mevalonate, an important precursor to the isoprenoid family of compounds, which includes pharmaceuticals, specialty chemicals, and potential biofuels (43, 44). We transformed a plasmid encoding a mevalonate synthesis pathway into E. coli MG1655 bearing pHipA and activated expression of the pathway before inducing HipA. Mevalonate production in HipA-arrested cells was surprisingly robust, continuing for 7 days (FIG. 11A). The mevalonate production rate per cell in the growth-arrested culture closely matched the rate observed in the nonarrested culture [0.33±0.04 μg/h/($OD_{600}$·ml)] before declining slowly after the third day of production [0.23±0.04 μg/h/($OD_{600}$·ml) at 3.5 days]. Over 8 days, the HipA-arrested cells produced a final mevalonate titer approximately one-third that produced by growing cells (0.38±0.01 mg versus 1.15±0.07 mg produced by growing cells), which might have been due to translational inhibition in the HipA-arrested cells preventing the regeneration of pathway enzymes lost to proteolytic degradation or deactivation. In order to demonstrate that mevalonate production can be protected by HipA arrest from lysis by phage, we added phage P1vir to mevalonate-producing HipA-arrested cells and uninduced stationary-phase cells. Lysis was triggered by diluting the infected cultures into fresh medium, causing the stationary-phase cells to resume growth. After 2 days, phage infection decreased mevalonate production by nearly 50% in the nonarrested culture, while production by the HipA-arrested culture was unaffected (FIG. 11B). Absolute titers in the HipA-arrested cells were lower (232±44 μM for uninfected and 151±13 μM for phage-infected growing cells versus 22±2 μM for uninfected and 22±3 μM for phage-infected HipA-arrested cells) due to the low cell density of HipA-arrested cells.

Discussion

The mechanism by which a single protein kinase, HipA, affects so many cellular processes and causes growth arrest has been unknown since the discovery of the hipA gene 30 years ago (45). The finding that HipA phosphorylates EF-Tu in vitro has been thought to explain how HipA expression attenuates translation, while the inhibition of other processes has led to the proposal that HipA phosphorylates targets in addition to EF-Tu (9, 46). Our results do not preclude the possibility that there exist other protein targets for phosphorylation by HipA or that ppGpp induces further protective responses. However, we find that ppGpp synthesis by RelA is necessary and sufficient for maintaining inhibition of DNA replication initiation, rRNA transcription, and β-lactam tolerance in HipA-arrested cells.

Inhibition of translation by HipA may also play some role in controlling DNA replication, as HipA expression within ΔrelA cells did not result in a large increase in intracellular DNA, seemingly contradicting the results obtained by chloramphenicol treatment. However, translational inhibition by an amino acid analog (serine hydroxamate), which induces ppGpp synthesis by RelA in wild-type cells, also does not cause a dramatic accumulation of DNA within ΔrelA cells (34). We suspect that while ppGpp inhibits DNA replication at defined points (namely, replication initiation [13, 47] and chromosome segregation), other factors also contribute to modulating the elongation stage of DNA synthesis. However, because serine hydroxamate is also unable to trigger runaway DNA synthesis in ΔrelA cells, our results do not imply a role for HipA in directly regulating DNA replication through any mechanism outside either ppGpp synthesis or translation inhibition. We also note that ppGpp may also contribute to the translational inhibition observed in HipA-arrested cells, as ppGpp itself directly inhibits protein synthesis (15), and the residual growth observed in HipA-expressing ΔrelA cultures may indicate that EF-Tu phosphorylation by HipA alone is not sufficient to completely inhibit translation.

While we have not determined the precise mechanism by which HipA expression leads to ppGpp biosynthesis by RelA, we speculate that inhibiting formation of the EF-Tu.GTP.aminoacyl-tRNA ternary complex blocks the primary route by which aminoacyl-tRNA is delivered to the A site of the ribosome. This allows deacylated tRNA to bind to unoccupied A sites, a process that is typically prevented during growth by EF-Tu-catalyzed delivery of aminoacyl-tRNA, which is far more rapid (48). Binding of deacyl-tRNA to the ribosomal A site triggers ppGpp biosynthesis by the enzyme RelA (49).

The dependence of HipA toxicity on ppGpp synthesis explains the susceptibility of HipA-arrested cells to aminoglycoside antibiotics (50), as aminoglycosides also suppress ppGpp synthesis (51). However, not all toxins found in *E. coli* trigger ppGpp synthesis, which implies that not all persister cells rely upon ppGpp to induce and sustain growth arrest. For instance, overexpression of the RNase toxin RelE in *E. coli* leads to a decrease in the ppGpp concentration (52). The molecular mechanisms by which the other toxins provide protection against antibiotic treatments remain unclear (3).

Our demonstration that chloramphenicol sensitizes HipA-arrested cells to β-lactam antibiotics implied to us that the protective effect of persistence could be directly eliminated by chemically inhibiting ppGpp biosynthesis. This would be consistent with a recent report that generation of persister cells within biofilms relies on the stringent response (ppGpp synthesis) (53). Unfortunately, we found that treating persister cells (as distinct from cells arrested by artificial HipA expression) with a β-lactam antibiotic in combination with chloramphenicol did not result in more efficient killing. This may have been due to the following possibilities.

1. ppGpp levels in naturally occurring persister cells are maintained in a way that is not affected by chloramphenicol.
2. While HipA is a bona fide toxin, it may be that it does not, in fact, contribute to the development of persister cells, at least under the conditions tested.
3. TA modules are highly redundant (6). Removal of more than five toxin/antitoxin modules was required before a reduction in the number of persisters generated could be detected. If HipA generated a small fraction of the total number of persister cells under the conditions we tested, their elimination would be difficult to detect.
4. HipA activity triggers ppGpp, which may then induce the development of persistence through the activation of other toxins which do not rely upon the maintenance of high ppGpp for antibiotic tolerance. It was recently shown that overexpression of HipA triggers the transcriptional activation of other TA modules (54).

While progress has been made in establishing the mechanisms by which toxins trigger growth arrest, how naturally activated toxins lead to persistence remains unclear. It may be that true persister cells arise only via the overlapping activation of multiple toxins with different activities rather than with a single toxin. Further studies will be required to determine which, if any, of these possibilities is correct.

ppGpp has been previously linked with persistence by Gerdes and Maisonneuve (4). In their model, ppGpp activates toxin expression indirectly by inhibiting the enzyme Ppx, which catalyzes the hydrolysis of intracellular polyphosphate. Inhibition of Ppx is expected to cause the buildup of polyphosphate, a signal that allosterically activates the protease Lon. Because antitoxins are rapidly eliminated by Lon activity, toxin inhibition should be relieved. Our results demonstrate another link between persistence and ppGpp, indicating that toxin activity can use ppGpp to drive a global cellular response. Linking our results with the model proposed above, it is possible that HipA may activate other toxins in a cascade by initiating ppGpp synthesis. The activity of downstream toxins may be the basis of some of the stress-resistant phenotypes that are activated by ppGpp but that can be maintained without ppGpp, as alluded to above.

We found that artificial growth arrest induced by HipA leads to a suspended state of metabolism where carbon is still consumed but is not significantly directed to biomass accumulation, illustrating how cells continue to regulate their metabolism during a state of attenuated translation by relying on posttranslational mechanisms. Active metabolism of toxin-arrested cells has been observed previously, and has been used to direct the specific synthesis of proteins, using the RNase MazF (55). Here, we have shown that toxin-arrested cells can also render a culture resistant to phage. We acknowledge that toxin arrest would not completely eliminate the vulnerability of a production culture to phage attack, as the culture would still need to be grown to a high density, during which time it would be susceptible. However, once a high density of cells is established, toxin-arrested cultures could enable both phage- and antibiotic-resistant fermentation.

Example 2

Production of Car in *E. coli* by expression of the Car pathway from *Pectobacterium carotovora* has been previously demonstrated {McGowan, 1996 #1928}, however, to our knowledge, production of Car to the point of inducing lysis of the producing cells has not been seen. We transformed a plasmid encoding the Car biosynthesis pathway (codon-optimized carA, carB, and carC genes), into *E. coli* BL21 cells bearing a plasmid encoding the HipA toxin. The Car pathway was induced using IPTG, after which HipA expression was induced using anhydrous tetracycline, and cells were incubated for 24 hours. In cells expressing Car, we observed lysis, whereas cells expressing HipA and Car did not lyse. Furthermore, a compound with the exact mass as the hydrolyzed Car (an unstable compound) was detected using mass spectrometry (MS). Cells expressing a partial pathway did not show any lysis whatsoever, nor was any sign of Car detected.

In some embodiments, the invention provides for the utility of growth-arrested bacterial cells for the synthesis of valuable products that may be toxic to growing cells. This can be done by: (1) applying traditional metabolic engineering approaches to improve the production of Car by growth-arrested cells; (2) using growth-arrested cells as in vivo testing platforms to elucidate the role of specific enzymes in the thienamycin pathway and built upon advances to produce thienamycin at high titers; and (3) demonstrate the usefulness of growth-arrested cells as whole-cell biocatalysts for the modification of beta-lactam antibiotics.

Improve Production of Car by HipA-Arrested Cells Through Metabolic Engineering.

In some embodiments, the invention provides for increasing production of the simple carbapenem Car during HipAprogrammed growth arrest. This will demonstrate the applicability of established engineering principles to growth-arrested cells, and provide a template to follow for pathway optimization for other toxic compounds.

Increase P5C by Relieving Feedback Inhibition of Native Proline Pathway

Figure 3:
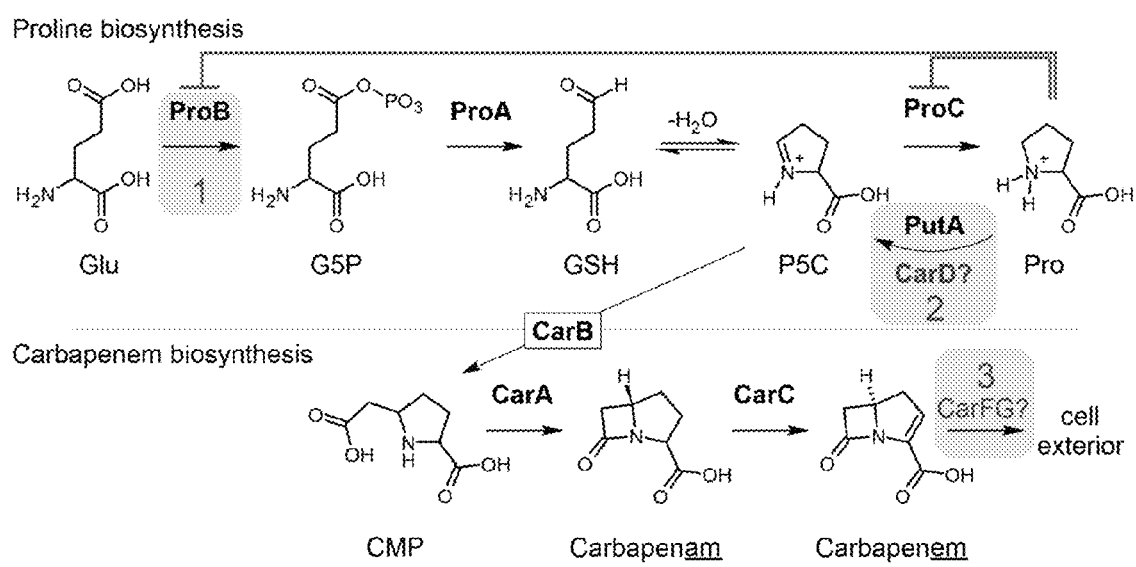
FIG. 3 shows the biosynthetic pathways of proline and carbapenem.

Pyrroline 5-carboxylate (P5C), an intermediate of the proline biosynthetic pathway, is used in the first step of Car biosynthesis by CarB, which generates carboxymethylproline (CMP) by condensing P5C with malonyl-CoA {Li, 2000 #1925}. P5C is generated from glutamate semialdehyde (GSH) via spontaneous dehydration (FIG. 3). GSH is in turn produced from glutamate by ProB (glutamate kinase), which is feedback-inhibited by proline {Perez-Arellano, 2005 #1924}. We have demonstrated that growth arrest by HipA leads to proline accumulation and strong inhibition of proline biosynthesis (likely by proline) in HipA-arrested cells {Bokinsky, 2013 #1896}, which is expected to deplete both GSH and P5C. Thus, we suspect inhibition of ProB and a lack of P5C are likely responsible for decreasing Car production during growth arrest.

We will restore GSH and P5C production during growth arrest by expressing feedback inhibition-resistant mutants of ProB, which has been shown to dramatically increase proline production in E. coli and other species {Jakowec, 1985 #1941; Omori, 1992 #1940}. Mutations in ProB, such as I53A, N134D, or E143A/K145A are known to relieve proline inhibition without substantially affecting activity {Perez-Arellano, 2010 #1891}. Using homologous recombination, we will replace the wild-type proB gene with genes encoding feedback-resistant proB mutants {Datsenko, 2000 #1944}. Increased proline and Car production can be verified by MS-based quantification {Bennett, 2008 #427}. We will also attempt to increase Car production further by overexpressing feedback-resistant ProB at high levels (e.g. from a high-copy plasmid).

Increase P5C by Expressing Putative Proline Oxidase Enzyme CarD

The P. carotovorum Car gene cluster encodes two proteins of unknown function, CarD and CarE. CarD has sequence homology to proline oxidase in Drosophila melanogaster, which catalyzes the first step in proline catabolism (conversion of proline to GSH, FIG. 3). Inactivation of CarD in P. carotovorum substantially decreases production of Car {McGowan, 1996 #1928}, suggesting a role in Car biosynthesis. In our hands, co-expression of both CarD and CarE with CarA, CarB, and CarC resulted in a 10-fold increase in Car titers. We will confirm the role of CarD by measuring the concentration of GSH and P5C in strains overexpressing CarD.

Optimize Timing of HipA and Car Pathway Expression

Expression of HipA leads to a growth arrest within approximately 45 minutes after induction {Bokinsky, 2013 #1896; Korch, 2006 #386}. For our pilot experiments, we have been inducing HipA 1-2 hours after induction of the full Car pathway. It is possible that this timing is not optimal, as HipA arrest inhibits translation and may prevent optimal expression of the Car proteins, or may restrict cell growth to a low density, which may be inefficient for purposes of high titer. We will optimize induction conditions (e.g. inducer concentrations), and the timing of the Car pathway and HipA expression in order to maximize Car titer.

However, it is possible that highly-active Car pathways will produce toxic levels of Car before HipA can arrest growth and confer tolerance to Car. In this event, we will express the Car pathway in stages. A partial Car pathway can be overexpressed early during growth. Once sufficient cell density is reached, the remaining enzymes of the Car pathway can be induced simultaneously with HipA. This will prevent production of Car until HipA expression has been triggered (FIG. 3). We have also noticed that translation continues in HipA-arrested cells, albeit at a reduced rate (~10%). If even co-expression with HipA is too slow to protect against highly-active Car pathways, we will induce the remaining pathway enzymes during HipA arrest, once Car tolerance is fully bestowed.

Demonstrate Production of Car in Benchtop Fermenter

Higher titers can be achieved by increasing the density of growth-arrested cells. We can induce Car production and growth arrest in cells cultured within a small (1-2 L) benchtop fermenter to demonstrate that growth-arrested cells are compatible with fermenters.

Produce Thienamycin by Expressing Genes from S. Cattleya and Other Thienamycin-Producing Species with Engineered Car Pathway.

Thienamycin, the first carbapenem compound discovered {Kahan, 1979 #1939}, is the basis for the entire family of carbapenem antibiotics. Despite extensive study, the biosynthetic pathway of thienamycin by Streptomyces cattleya is only partially understood. In this Goal, I propose to use growth-arrested E. coli as a platform for elucidating the functions of enzymes from the thienamycin biosynthetic pathway, while working towards a goal of high-titer thienamycin production. The microbial production of a powerful antibiotic at high titers would validate our approach as an method for generating carbapenem antibiotics at low cost. Our overall approach can be applied to other biosynthetic pathways that produce compounds toxic to the host. In some embodiments, the invention provides for a titer of at least about 100 mg/L.

Figure 4:
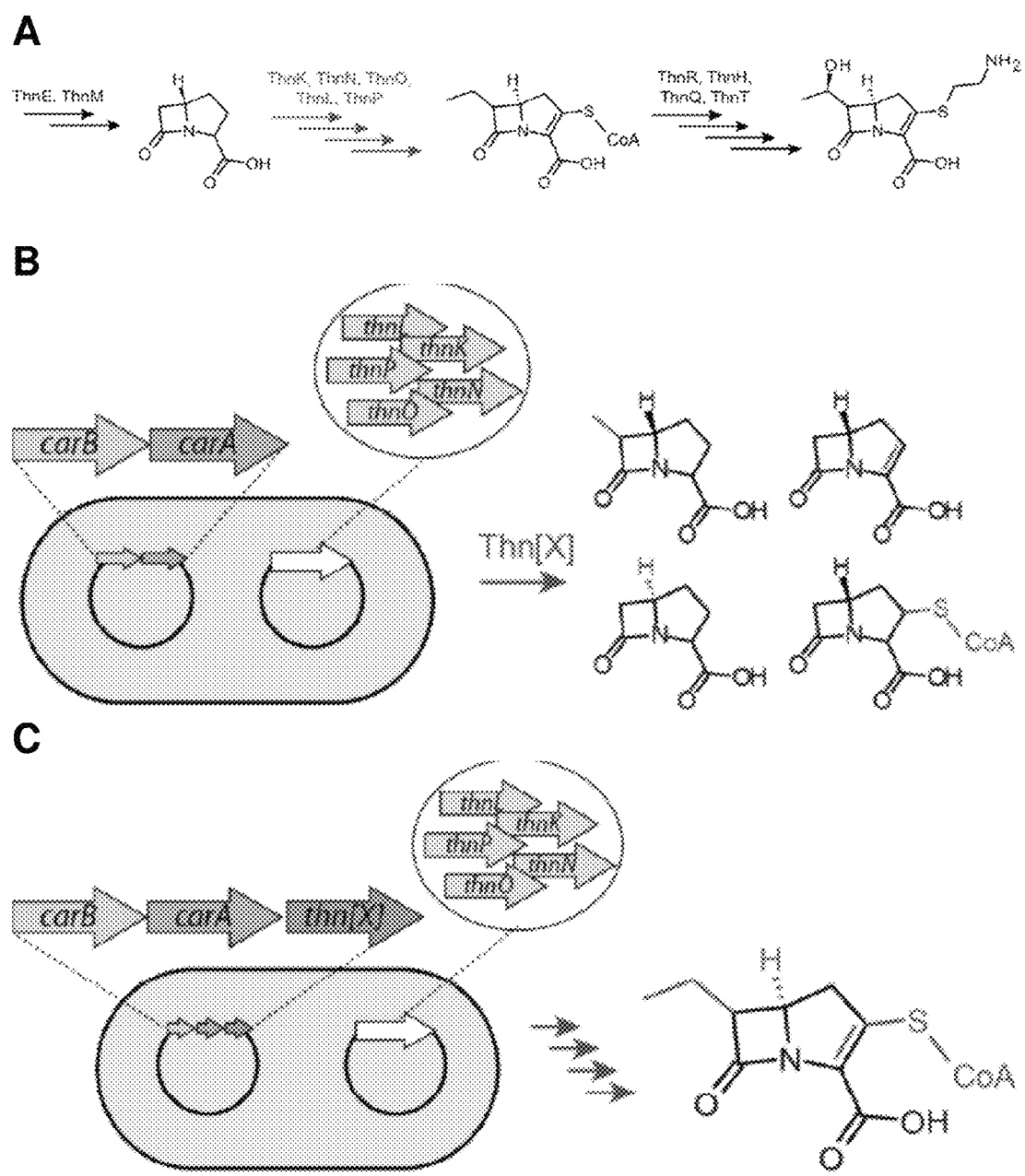
FIG. 4 shows the use of growth-arrested cells as a platform for elucidating the function of genes of the thn pathway. Panel (A): The thienamycin biosynthetic pathway in *S. cattleya*. The enzymes of unknown function that are thought to contribute to the pathway are ThnK, ThnN, ThnO, ThnL, and ThnP. Panel (B): thn genes of unknown functions are individually co-expressed with the carA and carB genes within growth-arrested *E. coli* cells and putative intermediate compounds are detected. Once a modified carbapenam (carbapenem) is detected, this indicates the selected gene encodes the enzyme that catalyzes the next step in the thienamycin pathway. Panel (C): Genes whose activities have been determined (thn[X]) are incorporated into the pathway and the remaining thn genes are screened for activity. The process is repeated until the activities of all thn genes are determined.

Identification of Catalytic Activities of Enzymes from Thienamycin Pathway by Co-Expression with Synthetic Car Pathway The S. cattleya thn gene cluster consists of 22 ORFs {Nunez, 2003 #1929}. While the functions of several of the enzymes encoded by the cluster have been identified {Bodner, 2011 #1930; Freeman, 2008 #1934; Rodriguez, 2011 #1936}, the enzymes that catalyze specific modifications crucial to the activity and stability of thienamycin remain unknown (FIG. 4). We can use our growth-arrested E. coli as a platform to determine the enzymes responsible for catalyzing these reactions, and in doing so, work towards building a synthetic pathway for thienamycin production.

While the initial steps of thienamycin synthesis are identical to the synthesis of Car, it is thought that the thienamycin pathway diverges after production of the simple carbapenam (FIG. 4). In order to determine which enzyme catalyzes the following reaction, we will express candidate genes thought to catalyze subsequent steps (thnK, thnN, thnO, thnL, and thnP) while expressing both CarA and CarB, which will provide the carbapenam intermediate (FIG. 4). All genes will be codon-optimized for expression in E. coli. We can detect which enzyme catalyzes the subsequent reaction by using LC/MS to determine if specific intermediates within the pathway are generated by co-expression with CarA and CarB. If we detect compounds corresponding to the molecular weight of expected intermediates, this will imply that the tested gene catalyzes the subsequent step in the pathway, establishing evidence for a specific role in thienamycin synthesis.

We will incorporate the gene into our cluster of genes of known function and continue to test the remaining enzymes for activity, building the complete thienamycin pathway in a stepwise manner (FIG. 4). We will also express enzymes from other thienamycin pathways from other species if the enzymes screened do not show activity. This approach will also enable us to produce the potent antibiotic thienamycin.

Generation of Thienamycin and Thienamycin Derivatives by Expression of Genes of Known Activity The generation of the cysteamine side chain on C2 of the Car core has been shown to proceed via incremental cleavage of CoA by ThnR, ThnH, and ThnT enzymes {Freeman, 2008 #1934}. ThnR and ThnH will be expressed to determine if they are active in vivo. Expression of ThnR is expected to result in production of 4-phosphopantetheine by cleavage of CoA. As 4-phosphopantetheine is a substrate of ThnH, co-expression of ThnR and ThnH is expected to yield pantetheine. We will attempt to measure the concentration of these compounds by extracting the compounds from ThnR and ThnH-expressing cells and detecting the compounds using LC-MS/MS. Once the thienamycin pathway up is known, ThnR, ThnH, and ThnT will be expressed to generate the cysteamine side chain, and ThnQ will be expressed to hydroxylate the ethyl side chain on C6, generating thienamycin. We will also attempt to generate N-acetyl thienamycin by expression of ThnF.

Demonstrate Use of Growth-Arrested Cells as Whole-Cell Biocatalysts for Modifications to Beta-Lactam Antibiotics.

The growing resistance to beta-lactam antibiotics requires further diversification of our arsenal. The use of enzymes to functionalize various beta-lactams has replaced many chemical steps that are costly and wasteful. However, the production of these enzymes, which requires overexpression, harvesting, purification, and immobilization at levels required for industrial processes, is also costly. A general solution to this problem is the use of whole-cell biocatalysts, in which cells expressing enzymes of the desired activity are used without lysis or harvesting to catalyze the reaction. Substrates of the reaction diffuse into the cell, are modified by the enzyme, and the products diffuse out. It could be highly desirable if whole-cell biocatalysts could be used for beta-lactam modification. However, the beta-lactam substrates and products are highly toxic to cells, and would trigger lysis. The use of metabolically-active growth-arrested cells may represent a possible solution that could enable the use of whole-cell microbial catalysts to engineer desired modifications in beta-lactams, avoiding the need for costly and laborious harvesting, purification, and immobilization of enzymes, as well as chemical reactants.

Demonstrate Effectiveness of Growth-Arrested Cells Expressing Penicillin G Acylase The enzyme penicillin G acylase (PGA), which has been found in many bacterial species, hydrolyzes penicillin G into phenylacetic acid and 6-aminopenicillanic acid (6-APA). PGA can also be used to catalyze the reverse reaction, appending various acyl groups to the amine group of 6-APA and generating a diverse library of semisynthetic penicillins (for a review, see {Srirangan, 2013 #1949}). Typically, PGA is obtained by overexpression within a bacterial host such as *E. coli*, where it is often subject to misfolding and degradation when expressed at high levels. When expressed, PGA often is localized to the periplasmic space. The optimization of downstream steps including extracting PGA from the cells, partial purification, and immobilization, is being intensively pursued {Aguilar, 2006 #1950; Orr, 2012 #1951}. However, the use of whole-cell catalysts could avoid these steps and enable a true one-pot reaction.

We will use our growth-arrested cells to determine if they can be used as whole-cell catalysts for the modification of penicillins using intracellular PGA. PGA will be overexpressed in *E. coli*, and growth arrested using HipA expression. The PGA-expressing arrested cells will be concentrated and mixed with penicillin G to determine if conversion to 6-APA can be achieved. If successful, we will next attempt to use this platform to mix 6-APA with various other esters to see if 6-APA can be modified using our cells into semisynthetic penicillins. We will determine the presence of modified compounds using LC/MS at all steps.

Use Growth-Arrested Cells as Biocatalysts Using Enzymes with Other Activities

The use of metabolically-active growth-arrested cells as whole-cell biocatalysts has other advantages. Many modifications require high-energy cofactors, such as ATP and acetyl-CoA, which are naturally present at high levels in HipA-arrested cells {Bokinsky, 2013 #1896}. We will demonstrate the advantages using other enzymes that modify penicillins that require these other cofactors. We will overexpress the expandase and acetyl transferase enzymes from *Acremonium chrysogenum* to determine if they are active against penicillin N as a substrate, to see if they can produce cephalosporin C and deacetoxycephalosporin C.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified host cell, comprising: (a) increased expression of a toxin of a toxin-antitoxin (TA) module, or a substantially identical polypeptide thereof, (b) increased expression of one or more enzymes of a pathway for the biosynthesis of an antibiotic that is toxic to the host cell when the host cell is growing; wherein the host cell is an *Escherichia coli* bacterium having an endogenous RelA.

2. The genetically modified host cell of claim 1, wherein the toxin is HipA, or a substantially identical polypeptide thereof.

3. The genetically modified host cell of claim 1, wherein the antibiotic is carbapenem, thienamycin, or penicillin.

4. A method of constructing a genetically modified host cell comprising (a) introducing a first vector encoding the toxin, or a substantially identical polypeptide thereof, operatively linked to a promoter capable of expressing the toxin in the host cell, one or more enzymes of a pathway for the biosynthesis of an antibiotic into a host cell; wherein the host cell is an *Escherichia coli* bacterium having an endogenous RelA.

5. The method of claim 4, further comprising (b) introducing a second vector encoding the one or more enzymes of the pathway for the biosynthesis of the antibiotic into the host cell operatively linked to one or more promoters capable of expressing the enzymes in the host cell.

6. The method of claim 4, wherein the toxin is HipA, or a substantially identical polypeptide thereof.

7. The method of claim 5, wherein the antibiotic is carbapenem, thienamycin, or penicillin.

8. A method of producing an antibiotic comprising:
(a) providing the genetically modified host cell of claim 1,
(b) arresting the growth of the host cell, and
(c) producing the antibiotic.

9. The method of claim 8, further comprising: introducing a first vector encoding the toxin, or a substantially identical polypeptide thereof, operatively linked to a promoter capable of expressing the toxin in the host cell, one or more enzymes of a pathway for the biosynthesis of an antibiotic into the host cell.

10. The method of claim 9, further comprising: introducing a second vector encoding the one or more enzymes of the pathway for the biosynthesis of the antibiotic into the host cell operatively linked to one or more promoters capable of expressing the enzymes in the host cell.

11. The method of claim 8, wherein the toxin is HipA, or a substantially identical polypeptide thereof.

12. The method of claim 8, wherein the antibiotic is carbapenem, thienamycin, or penicillin.

13. The genetically modified host cell of claim 2, wherein the substantially identical polypeptide of HipA has at least 70% sequence identity with the amino acid sequence of SEQ ID NO:1, and comprises one or more of the residues at positions 181, 309, 152-157, 234-236, 311-314, 331-314, 331-332, and 379-382 of SEQ ID NO:1.

14. The method of claim 6, wherein the substantially identical polypeptide of HipA has at least 70% sequence identity with the amino acid sequence of SEQ ID NO:1, and comprises one or more of the residues at positions 181, 309, 152-157, 234-236, 311-314, 331-314, 331-332, and 379-382 of SEQ ID NO:1.

* * * * *

SEQUENCE LISTING

<160> NUMBER OF SEQ ID NOS: 1

<210> SEQ ID NO 1
<211> LENGTH: 440
<212> TYPE: PRT
<213> ORGANISM: Escherichia coli

<400> SEQUENCE: 1

Met Pro Lys Leu Val Thr Trp Met Asn Asn Gln Arg Val Gly Glu Leu
1               5                   10                  15

Thr Lys Leu Ala Asn Gly Ala His Thr Phe Lys Tyr Ala Pro Glu Trp
            20                  25                  30

```
Leu Ala Ser Arg Tyr Ala Arg Pro Leu Ser Leu Ser Leu Pro Leu Gln
         35                  40                  45

Arg Gly Asn Ile Thr Ser Asp Ala Val Phe Asn Phe Phe Asp Asn Leu
 50                  55                  60

Leu Pro Asp Ser Pro Ile Val Arg Asp Arg Ile Val Lys Arg Tyr His
65                   70                  75                  80

Ala Lys Ser Arg Gln Pro Phe Asp Leu Leu Ser Glu Ile Gly Arg Asp
                 85                  90                  95

Ser Val Gly Ala Val Thr Leu Ile Pro Glu Asp Glu Thr Val Thr His
            100                 105                 110

Pro Ile Met Ala Trp Glu Lys Leu Thr Glu Ala Arg Leu Glu Glu Val
        115                 120                 125

Leu Thr Ala Tyr Lys Ala Asp Ile Pro Leu Gly Met Ile Arg Glu Glu
    130                 135                 140

Asn Asp Phe Arg Ile Ser Val Ala Gly Ala Gln Glu Lys Thr Ala Leu
145                 150                 155                 160

Leu Arg Ile Gly Asn Asp Trp Cys Ile Pro Lys Gly Ile Thr Pro Thr
                165                 170                 175

Thr His Ile Ile Lys Leu Pro Ile Gly Glu Ile Arg Gln Pro Asn Ala
            180                 185                 190

Thr Leu Asp Leu Ser Gln Ser Val Asp Asn Glu Tyr Tyr Cys Leu Leu
        195                 200                 205

Leu Ala Lys Glu Leu Gly Leu Asn Val Pro Asp Ala Glu Ile Ile Lys
    210                 215                 220

Ala Gly Asn Val Arg Ala Leu Ala Val Glu Arg Phe Asp Arg Arg Trp
225                 230                 235                 240

Asn Ala Glu Arg Thr Val Leu Leu Arg Leu Pro Gln Glu Asp Met Cys
                245                 250                 255

Gln Thr Phe Gly Leu Pro Ser Ser Val Lys Tyr Glu Ser Asp Gly Gly
            260                 265                 270

Pro Gly Ile Ala Arg Ile Met Ala Phe Leu Met Gly Ser Ser Glu Ala
        275                 280                 285

Leu Lys Asp Arg Tyr Asp Phe Met Lys Phe Gln Val Phe Gln Trp Leu
    290                 295                 300

Ile Gly Ala Thr Asp Gly His Ala Lys Asn Phe Ser Val Phe Ile Gln
305                 310                 315                 320

Ala Gly Gly Ser Tyr Arg Leu Thr Pro Phe Tyr Asp Ile Ile Ser Ala
                325                 330                 335

Phe Pro Val Leu Gly Gly Thr Gly Ile His Ile Ser Asp Leu Lys Leu
            340                 345                 350

Ala Met Gly Leu Asn Ala Ser Lys Gly Lys Lys Thr Ala Ile Asp Lys
        355                 360                 365

Ile Tyr Pro Arg His Phe Leu Ala Thr Ala Lys Val Leu Arg Phe Pro
    370                 375                 380

Glu Val Gln Met His Glu Ile Leu Ser Asp Phe Ala Arg Met Ile Pro
385                 390                 395                 400

Ala Ala Leu Asp Asn Val Lys Thr Ser Leu Pro Thr Asp Phe Pro Glu
                405                 410                 415

Asn Val Val Thr Ala Val Glu Ser Asn Val Leu Arg Leu His Gly Arg
            420                 425                 430

Leu Ser Arg Glu Tyr Gly Ser Lys
        435                 440
```